(12) United States Patent
Kitagawa et al.

(10) Patent No.: US 8,920,788 B2
(45) Date of Patent: Dec. 30, 2014

(54) HIGH-MOLECULAR WEIGHT CONJUGATE OF PHYSIOLOGICALLY ACTIVE SUBSTANCES

(75) Inventors: Masayuki Kitagawa, Tokyo (JP); Chieko Seno, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/922,747

(22) PCT Filed: Mar. 17, 2009

(86) PCT No.: PCT/JP2009/055115
§ 371 (c)(1),
(2), (4) Date: Dec. 8, 2010

(87) PCT Pub. No.: WO2009/116509
PCT Pub. Date: Sep. 24, 2009

(65) Prior Publication Data
US 2011/0201754 A1 Aug. 18, 2011

(30) Foreign Application Priority Data
Mar. 18, 2008 (JP) ................................. 2008-069067

(51) Int. Cl.
| | | |
|---|---|---|
| *A61K 31/74* | (2006.01) | |
| *A61K 31/352* | (2006.01) | |
| *A61K 31/197* | (2006.01) | |
| *A61K 31/405* | (2006.01) | |
| *A61K 31/407* | (2006.01) | |
| *A61K 31/704* | (2006.01) | |
| *A61K 47/48* | (2006.01) | |
| *C08G 69/10* | (2006.01) | |
| *C08G 69/40* | (2006.01) | |
| *C08G 69/48* | (2006.01) | |

(52) U.S. Cl.
CPC ............. *A61K 31/352* (2013.01); *A61K 31/197* (2013.01); *A61K 31/405* (2013.01); *A61K 31/407* (2013.01); *A61K 31/704* (2013.01); *A61K 47/48215* (2013.01); *A61K 47/48315* (2013.01); *C08G 69/10* (2013.01); *C08G 69/40* (2013.01); *C08G 69/48* (2013.01)
USPC ........ 424/78.17; 424/486; 525/403; 525/408; 525/419; 525/449; 528/310; 528/328

(58) Field of Classification Search
USPC ............... 424/486, 78.17; 525/403, 408, 419, 525/449; 528/310, 328
See application file for complete search history.

(56) References Cited

U.S. PATENT DOCUMENTS

| | | |
|---|---|---|
| 3,979,449 A | 9/1976 | Hirsbrunner et al. |
| 4,734,512 A | 3/1988 | Kaneko et al. |
| 4,892,733 A | 1/1990 | Bichon et al. |
| 5,037,883 A | 8/1991 | Kopecek et al. |
| 5,182,203 A | 1/1993 | Ebersole et al. |
| 5,412,072 A | 5/1995 | Sakurai et al. |
| 5,438,072 A | 8/1995 | Bobee |
| 5,510,103 A | 4/1996 | Yokoyama et al. |
| 5,552,517 A | 9/1996 | Martin |
| 5,571,889 A | 11/1996 | Katoh et al. |
| 5,614,549 A | 3/1997 | Greenwald et al. |
| 5,639,832 A | 6/1997 | Kroner et al. |
| 5,693,751 A | 12/1997 | Sakurai et al. |
| 5,877,205 A | 3/1999 | Andersson |
| 5,985,548 A | 11/1999 | Collier et al. |
| 6,025,385 A | 2/2000 | Shimizu et al. |
| 6,153,655 A | 11/2000 | Martinez et al. |
| 6,262,107 B1 | 7/2001 | Li et al. |
| 6,322,817 B1 | 11/2001 | Maitra et al. |
| 6,376,470 B1 | 4/2002 | Greenwald et al. |
| 6,410,731 B2 | 6/2002 | Curran et al. |
| 6,458,347 B1 | 10/2002 | Sugawara et al. |
| 6,573,284 B1 | 6/2003 | Riley et al. |
| 6,596,757 B1 | 7/2003 | Chari et al. |
| 6,713,454 B1 | 3/2004 | Ekwuribe et al. |
| 6,720,304 B1 | 4/2004 | Sinn et al. |

(Continued)

FOREIGN PATENT DOCUMENTS

| | | |
|---|---|---|
| CA | 2383240 A1 | 3/2001 |
| CA | 2334615 A1 | 8/2001 |

(Continued)

OTHER PUBLICATIONS

O'Neill, M.J. et al.; The Merck Index, 2006, p. 1-16.*

(Continued)

*Primary Examiner* — Robert Jones, Jr.
(74) *Attorney, Agent, or Firm* — Nields, Lemack & Frame, LLC

(57) ABSTRACT

Disclosed is a water-soluble high-molecular weight conjugate of physiologically active substances which enable medicament to release without depending on the enzymes in a living body and which is expected to have a useful therapeutic effect. A high-molecular weight conjugate of a physiologically active substance has a substituent group represented by a general formula (1) bonded to a side-chain carboxy group of a block copolymer which has a polyethylene glycol moiety and either a polyaspartic acid moiety or a polyglutamic acid moiety. Formula (1): —Ar—CR15R16-O—C(=O)-A [In the formula: Ar represents an aromatic hydrocarbon group optionally a substituent group, or an aromatic heterocyclic group optionally having a substituent group; R15 and R16 independently represent a hydrogen atom or a (C1-C6) alkyl group optionally having a substituent group; and A represents a residual group of a physiologically active substance that has an carboxy group, or a residual group of a physiologically active substance that has an amino group].

18 Claims, 2 Drawing Sheets

(56) References Cited

U.S. PATENT DOCUMENTS

| | | | |
|---|---|---|---|
| 6,720,306 | B2 | 4/2004 | Greenwald et al. |
| 6,858,582 | B2 | 2/2005 | Yatvin et al. |
| 7,138,490 | B2 | 11/2006 | Nakanishi et al. |
| 7,176,185 | B2 | 2/2007 | Hilfinger et al. |
| 7,495,099 | B2 | 2/2009 | Kitagawa et al. |
| 7,700,709 | B2 | 4/2010 | Masuda et al. |
| 7,820,759 | B2 | 10/2010 | Shimizu et al. |
| 8,188,222 | B2 | 5/2012 | Yamamoto et al. |
| 8,323,669 | B2 | 12/2012 | Kitagawa et al. |
| 8,334,364 | B2 | 12/2012 | Yamamoto et al. |
| 8,703,878 | B2 | 4/2014 | Kitagawa et al. |
| 8,808,749 | B2 | 8/2014 | Kitagawa et al. |
| 2001/0003779 | A1 | 6/2001 | Curran et al. |
| 2001/0014354 | A1 | 8/2001 | Yokoyama et al. |
| 2001/0041189 | A1 | 11/2001 | Xu |
| 2002/0009426 | A1 | 1/2002 | Greenwald et al. |
| 2002/0016285 | A1 | 2/2002 | Bhatt et al. |
| 2002/0099013 | A1 | 7/2002 | Piccariello et al. |
| 2002/0119951 | A1 | 8/2002 | Seyedi et al. |
| 2002/0161062 | A1 | 10/2002 | Biermann et al. |
| 2002/0183259 | A1 | 12/2002 | Choe et al. |
| 2003/0032593 | A1 | 2/2003 | Wender et al. |
| 2003/0054977 | A1 | 3/2003 | Kumar et al. |
| 2003/0149003 | A1 | 8/2003 | Chaplin et al. |
| 2005/0054026 | A1* | 3/2005 | Atsushi et al. ............ 435/23 |
| 2005/0119193 | A1 | 6/2005 | Motoyama |
| 2005/0147617 | A1 | 7/2005 | Ji et al. |
| 2005/0171036 | A1* | 8/2005 | Arakawa et al. ........... 514/43 |
| 2006/0009622 | A1* | 1/2006 | Fuselier et al. .......... 530/402 |
| 2006/0057219 | A1 | 3/2006 | Nagasaki et al. |
| 2006/0067910 | A1 | 3/2006 | Kitagawa et al. |
| 2006/0099265 | A1 | 5/2006 | Shimizu et al. |
| 2006/0233883 | A1 | 10/2006 | Ishihara et al. |
| 2006/0258569 | A1 | 11/2006 | McTavish |
| 2007/0004674 | A1 | 1/2007 | Shiotsu et al. |
| 2007/0196497 | A1 | 8/2007 | Pouliquen et al. |
| 2008/0113028 | A1 | 5/2008 | Shimizu et al. |
| 2008/0145432 | A1 | 6/2008 | Kakizawa et al. |
| 2008/0221062 | A1 | 9/2008 | Miyamoto et al. |
| 2008/0269218 | A1 | 10/2008 | Kuramochi et al. |
| 2008/0280937 | A1 | 11/2008 | Leamon et al. |
| 2009/0012252 | A1 | 1/2009 | Masuda et al. |
| 2009/0156742 | A1 | 6/2009 | Shimizu et al. |
| 2009/0162313 | A1 | 6/2009 | Kitagawa et al. |
| 2009/0239782 | A1 | 9/2009 | Nakamura et al. |
| 2009/0275732 | A1 | 11/2009 | Hirotsu et al. |
| 2009/0281300 | A1 | 11/2009 | Yamamoto et al. |
| 2010/0004403 | A1 | 1/2010 | Kitagawa et al. |
| 2010/0029849 | A1 | 2/2010 | Yamamoto et al. |
| 2010/0234537 | A1 | 9/2010 | Kitagawa et al. |
| 2010/0292414 | A1 | 11/2010 | Kitagawa et al. |
| 2011/0136990 | A1 | 6/2011 | Harada et al. |
| 2011/0294980 | A1 | 12/2011 | Nakanishi et al. |
| 2012/0116051 | A1 | 5/2012 | Kitagawa et al. |
| 2013/0331517 | A1 | 12/2013 | Yamamoto et al. |
| 2014/0024703 | A1 | 1/2014 | Shimizu et al. |
| 2014/0142167 | A1 | 5/2014 | Shimizu et al. |
| 2014/0288244 | A1 | 9/2014 | Yamamoto et al. |

FOREIGN PATENT DOCUMENTS

| | | | |
|---|---|---|---|
| CN | 1307866 | A | 8/2001 |
| CN | 1708540 | A | 12/2005 |
| CN | 1800238 | A | 7/2006 |
| EP | 0397307 | A2 | 11/1990 |
| EP | 0583955 | A2 | 2/1994 |
| EP | 0757049 | A1 | 2/1997 |
| EP | 1127570 | A2 | 8/2001 |
| EP | 1580216 | A1 | 9/2005 |
| EP | 1857446 | A1 | 11/2007 |
| JP | 61-243026 | A | 10/1986 |
| JP | 62-96088 | A | 5/1987 |
| JP | 62-145093 | A | 6/1987 |
| JP | 63-10789 | A | 1/1988 |
| JP | 63-23884 | A | 2/1988 |
| JP | 63-502037 | A | 8/1988 |
| JP | 64-61422 | A | 3/1989 |
| JP | 64-61423 | A | 3/1989 |
| JP | 2-300133 | A | 12/1990 |
| JP | 5000955 | A | 1/1993 |
| JP | 5-117385 | A | 5/1993 |
| JP | 6-107565 | A | 4/1994 |
| JP | 6-206815 | A | 7/1994 |
| JP | 6-206830 | A | 7/1994 |
| JP | 6-206832 | A | 7/1994 |
| JP | 6-329085 | A | 11/1994 |
| JP | 8-48766 | A | 2/1996 |
| JP | 8-503689 | H | 4/1996 |
| JP | 8-507558 | A | 8/1996 |
| JP | 8-310970 | A | 11/1996 |
| JP | 2694923 | B1 | 12/1997 |
| JP | 10-513187 | H | 12/1998 |
| JP | 11-335267 | A | 12/1999 |
| JP | 2000-515132 | A | 11/2000 |
| JP | 2000-516948 | A | 12/2000 |
| JP | 2000-517304 | A | 12/2000 |
| JP | 2001-226294 | A | 8/2001 |
| JP | 2002-69184 | A | 3/2002 |
| JP | 2002-508400 | A | 3/2002 |
| JP | 3268913 | B2 | 3/2002 |
| JP | 2002-512265 | A | 4/2002 |
| JP | 3310000 | B2 | 7/2002 |
| JP | 2003-509385 | A | 3/2003 |
| JP | 2003-509386 | A | 3/2003 |
| JP | 2003-511349 | A | 3/2003 |
| JP | 2003-511423 | A | 3/2003 |
| JP | 2003-524028 | A | 8/2003 |
| JP | 2003-525238 | A | 8/2003 |
| JP | 2003-527443 | A | 9/2003 |
| JP | 2003-342167 | A | 12/2003 |
| JP | 2003-342168 | A | 12/2003 |
| JP | 2003-342269 | A | 12/2003 |
| JP | 2004-530736 | A | 10/2004 |
| JP | 2004-532289 | A | 10/2004 |
| JP | 2005-507912 | A | 3/2005 |
| JP | 2005-508832 | A | 4/2005 |
| JP | 2005-517675 | A | 6/2005 |
| JP | 2005-519122 | A | 6/2005 |
| JP | 2005-533026 | A | 11/2005 |
| JP | 2006-510627 | A | 3/2006 |
| JP | 2006-511571 | A | 4/2006 |
| JP | 2006-517572 | A | 7/2006 |
| JP | 2006-521367 | A | 9/2006 |
| JP | 2006-524673 | A | 11/2006 |
| JP | 2007-511586 | A | 5/2007 |
| JP | 2007-191643 | A | 8/2007 |
| WO | 93/24476 | A1 | 12/1993 |
| WO | 96/23794 | A1 | 8/1996 |
| WO | 97/38727 | A1 | 10/1997 |
| WO | 98/02426 | A1 | 1/1998 |
| WO | 98/07713 | A1 | 2/1998 |
| WO | 98/08489 | A1 | 5/1998 |
| WO | 99/30727 | A1 | 6/1999 |
| WO | 99/53951 | A1 | 10/1999 |
| WO | 01/19361 | A2 | 3/2001 |
| WO | 01/19406 | A2 | 3/2001 |
| WO | 01/19407 | A2 | 3/2001 |
| WO | 01/26693 | A2 | 4/2001 |
| WO | 01/64198 | A2 | 9/2001 |
| WO | 01/70275 | A2 | 9/2001 |
| WO | 01/92584 | A1 | 12/2001 |
| WO | 02/06279 | A1 | 1/2002 |
| WO | 02/065986 | A2 | 8/2002 |
| WO | 02/065988 | A2 | 8/2002 |
| WO | 02/066066 | A1 | 8/2002 |
| WO | 03/000771 | A1 | 1/2003 |
| WO | 03/035008 | A2 | 5/2003 |
| WO | 03/055860 | A1 | 7/2003 |
| WO | 2004/039869 | A1 | 5/2004 |
| WO | 2004/050087 | A1 | 6/2004 |
| WO | 2004/056782 | A1 | 7/2004 |
| WO | 2004/072051 | A1 | 8/2004 |
| WO | 2004/082718 | A1 | 9/2004 |

(56) References Cited

FOREIGN PATENT DOCUMENTS

| | | |
|---|---|---|
| WO | 2004/096212 A1 | 11/2004 |
| WO | 2005/000300 A1 | 1/2005 |
| WO | 2005/018674 A1 | 3/2005 |
| WO | 2005/066214 A1 | 7/2005 |
| WO | 2006/033296 A1 | 3/2006 |
| WO | 2006/055670 A2 | 5/2006 |
| WO | 2006/055760 A1 | 5/2006 |
| WO | 2006/095668 A1 | 9/2006 |
| WO | 2006/095783 A1 | 9/2006 |
| WO | 2006/101052 A1 | 9/2006 |
| WO | 2006/115293 A1 | 11/2006 |
| WO | 2006/120914 A | 11/2006 |
| WO | 2007/022493 A2 | 2/2007 |
| WO | 2007/080898 A1 | 7/2007 |
| WO | 2007/111211 A1 | 10/2007 |
| WO | 2007/135910 A1 | 11/2007 |
| WO | 2008/010463 A1 | 1/2008 |
| WO | 2008/041610 A1 | 4/2008 |
| WO | 2008/056596 A1 | 5/2008 |
| WO | 2008/056654 A1 | 5/2008 |
| WO | 2009/041570 A1 | 4/2009 |
| WO | 2009/142326 A1 | 11/2009 |
| WO | 2010/131675 A1 | 11/2010 |

OTHER PUBLICATIONS

Chinese Communication, with English translation, dated Oct. 10, 2011 in co-pending Chinese Patent Application No. 200880109404.7.
Office Action dated Dec. 15, 2011 in co-pending U.S. Appl. No. 11/662,834.
Nakanishi, "Development of the Polymer micelle carrier system for doxorubicin", Journal of Controlled Release (2001) vol. 74, No. 1-3, pp. 295-302, paragraph of "2. Structure of NK911".
Japanese International Search Report, dated Jun. 23, 2009.
International Search Report dated Dec. 24, 2003 in international patent application No. PCT/JP03/13838 (now USP 7,495,099).
Taiwanese Communication dated Nov. 30, 2006 in international patent application No. TW092130275 (now USP 7,495,099).
Russian Communication dated Apr. 20, 2007 in international patent application No. RU2005116309 (now USP 7,495,099).
European Communication dated Sep. 25, 2008 in international patent application No. EP03769949.3 (now USP 7,495,099).
International Search Report dated May 11, 2004 in co-pending international patent application No. PCT/JP2004/003647.
Chinese Communicaton dated Oct. 20, 2006 in co-pending international patent application No. CN200480007329.5.
Russian Communication dated Jun. 27, 2007 in co-pending international patent application No. RU2005132309/04.
European Communication dated Feb. 17, 2009 in co-pending international patent application No. EP04721673.4.
Chinese Communication, with English translation, dated Apr. 17, 2009 in co-pending international patent application No. CN200480007329.5.
European Communication dated Jun. 5, 2009 in co-pending international patent application No. EP04721673.4.
Korean Communication dated Nov. 8, 2010 in co-pending international patent application No. 10-2005-7017245.
International Search Report dated Nov. 15, 2005 in co-pending international patent application No. PCT/JP2005/017127.
Taiwanese Communication dated Jul. 22, 2011 in co-pending Taiwanese patent application No. 094132581.
International Search Report dated Jul. 25, 2006 in international patent application No. PCT/JP2006/308826 (now USP 7,700,709).
International Search Report dated May 15, 2007 in co-pending international patent application No. PCT/JP2007/055809.
International Search Report dated Aug. 21, 2007 in co-pending international patent application No. PCT/JP2007/060026.
European Communication dated Oct. 23, 2009 in co-pending international patent application No. EP07743461.1.
Chinese Communication, with English translation, dated Aug. 11, 2010 in co-pending international patent application No. CN2007800177809.
Russian Communication, with English translation, dated May 16, 2011 in co-pending international patent application No. RU2008149932/04.
International Search Report dated Oct. 16, 2007 in co-pending international patent application No. PCT/JP2007/063990.
Chinese Communication dated Nov. 10, 2010 in co-pending international application No. CN 200780027210.8.
International Search Report dated Jan. 8, 2008 in co-pending international patent application No. PCT/JP2007/068841.
Taiwanese Communication, with English translation, dated Dec. 14, 2011 in co-pending Taiwanese Application No. 094132581.
International Search Report dated Aug. 10, 2010 in co-pending PCT application No. PCT/JP2010/058034.
Final Rejection dated Feb. 16, 2012 in co-pending U.S. Appl. No. 12/226,962.
Office Action dated Feb. 21, 2012 in co-pending U.S. Appl. No. 12/312,009.
Notice of Allowance dated Mar. 1, 2012 in co-pending U.S. Appl. No. 12/312,157.
European Communication mailed Jan. 27, 2012 in co-pending European Patent Application No. 07831039.8.
Antimicrobial Agents and Chemotherapy, vol. 2, No. 5, Nov. 1972, pp. 395-401, XP 55016709, ISSN: 0066-4804, "Antiviral Action of Camptothecin", Horwitz, et al.
Chinese Communication, with English translation, dated Aug. 31, 2011 in corresponding Chinese patent application No. 200980110087.5.
International Search Report dated Jan. 29, 2008 in co-pending international patent application No. PCT/JP2007/071305.
International Search Report dated Jan. 29, 2008 in co-pending international patent application No. PCT/JP2007/071532.
International Search Report dated Dec. 9, 2008 in co-pending international patent application No. PCT/JP2008/067413.
Office Action dated Jan. 21, 2009 in co-pending U.S. Appl. No. 10/548,998.
Office Action dated Apr. 17, 2009 in co-pending U.S. Appl. No. 10/548,998.
Office Action dated Jul. 10, 2009 in co-pending U.S. Appl. No. 10/548,998.
Final Rejection dated Mar. 4, 2010 in co-pending U.S. Appl. No. 10/548,998.
Office Action dated Aug. 24, 2010 in co-pending U.S. Appl. No. 11/662,834.
Office Action dated Nov. 12, 2010 in co-pending U.S. Appl. No. 11/662,834.
Final Rejection dated Jun. 8, 2011 in co-pending U.S. Appl. No. 11/662,834.
Office Action dated Jun. 16, 2011 in co-pending U.S. Appl. No. 12/225,230.
Office Action dated Sep. 9, 2011 in co-pending U.S. Appl. No. 12/226,962.
Office Action dated Jul. 21, 2010 in abandoned U.S. Appl. No. 12/309,061.
Final Rejection dated Feb. 28, 2011 in abandoned U.S. Appl. No. 12/309,061.
Office Action dated Apr. 4, 2011 in co-pending U.S. Appl. No. 12/311,086.
Final Rejection dated Jul. 27, 2011 in co-pending U.S. Appl. No. 12/311,086.
Course for Universities, Third Edition, Revised and supplemented, "Visshaja Shkola" Publishing House, 1981, 656 pages, see p. 265, "High-Molecular Weight Compounds", SHUR.
6001 Chemical Abstracts, American Chemical Society, US, vol. 132, No. 2, Oct. 1, 2000, XP-002168038, 1 page abstract, "Polymer Micelle Compositions Containing Poorly Water-Soluble Drugs and their Preparation", Ichiro, et al.
Merriam-Webster's Collegiate Dictionary—11th Edition, 2004, 22 pages.
J. Org. Chem 2001, 66, 8135-8138, "Novel Syntheses of Cis and Trans Isomers of Combretastatin A-4", Gaukroger, et al.

(56) References Cited

OTHER PUBLICATIONS

Anti Cancer Drug Design, vol. 14, No. 6, Dec. 1999, ISSN 0266-9536, pp. 539-548, "Synthesis and antitumor activities of amino acid prodrugs of amino-combretastatins", Ohsumi, et al.
Journal of Pharmaceutical Sciences, vol. 92, No. 7, Jul. 2003, pp. 1343-1355, "MiniReview—Amphiphilic Block Copolymers for Drug Delivery", Adams, et al.
Chemistry and Biology, vol. 11, 787-797, Jun. 2004, "Targeting Wide-Range Oncogenic Transformation via PU24FCl, a Specific Inhibitor of Tumor Hsp90", Vilenchik, et al.
Trends in Molecular Medicine, vol. 8, No. 4, (Supp.) 2002, p. S55-61, "Hsp90 Inhibitors as Novel Cancer Chemotherapeutic Agents", Neckers, et al.
Current Cancer Drug Targets, 2003, vol. 3, 385-390, "The Clinical Applications of Heat Shock Protein Inhibitors in Cancer—Present and Future", Banerji, et al.
Cancer Science, Feb. 2004, V. 95, No. 2, 105-111, "Antitumor Activity of Sugar-Modified Cytosine Nucleosides", Matsuda, et al.
Cancer Research vol. 44, Jan. 25-30, 1984, "Antitumor Activity of 1-B-D-Arabinofuranosylcytosine Conjugated with Polyglutamic Acid and its Derivative", Kato, et al.
Journal of Controlled Release vol. 79 (2002), 55-70, "Anticancer Drug Delivery Systems: Multi-Loaded N4-acyl poly (ethylene glycol) prodrugs of ara-C. II. Efficacy in ascites and solid tumors", Choe, et al.
J.of Pharmacokinetics and BioPharmaceutics, vol. 23, No. 4, 1995, pp. 397-406, "In Vivo Pharmacokinetic Study for the Assessment of Poly(L-Aspartic Acid) as a Drug Carrier for Colon-Specific Drug Delivery", Leopold, et al.
Advanced Drug Delivery Reviews, vol. 20, (1996), 195-201, "Limethason as a lipid microsphere preparation: An Overview", Yokoyama, et al.
Journal of Peptide Science, vol. 3 (1997), 141-144, "Evaluation of Carbodiimides Using a Competition Method", Izdebski, et al.
Bioorganic & Medicinal Chemistry Letters, 2005, vol. 15, 3338-3343, "The identification, synthesis, protein crystal structure and in vitro biochemical evaluation of a new 3,4-diarylpyrazole class of Hsp90 inhibitors", Cheung, et al.
Molecular Cancer Therapeutics 2006, vol. 5, 1628-1637, "Preclinical pharmacokinetics and metabolism of a novel diaryl pyrazole resorcinol series of heat shock protein 90 inhibitors", Smith, et al.
Registry Entry for Registry No. 171009-07-07, which entered STN on Dec. 6, 1995, 3 pages.
Registry Entry for Registry No. 7689-03-4, which entered STN on Nov. 16, 1984, 3 pages.
Merriam Webster Online Dictionary entry for "Derivative", (http://www.merriam-webster.com/dictionary/derivative), last accessed Feb. 9, 2011, 3 pages.
Office Action dated Oct. 12, 2011 in co-pending U.S. Appl. No. 12/312,157.
Chinese Communication, with English translation, dated Sep. 23, 2011 in co-pending Chinese patent application No. 2007800177809.
International Search Report, dated Jul. 21, 2009 in co-pending PCT application No. PCT/JP2009/058325.
Final Rejection dated Nov. 8, 2011 in co-pending U.S. Appl. No. 12/225,230.
Office Action dated Oct. 25, 2011 in co-pending U.S. Appl. No. 12/312,009.
Colloids and Surfaces B: Biointerfaces V 16 (1999) pp. 217-226, "Micelle-like structures of poly(ethyleneoxide)-block-poly(2-hydroxyethyl aspartamide)-methotrexate conjugates", Li, et al.
Pharmaceutical Research, V. 17, No. 5 (2000) pp. 607-611, "Methotrexate Esters of Poly(EthyleneOxide)-Block-Poly (2-Hydroxyethyl-L-Aspartamide). Part I: Effects of the Level of Methotrexate Conjugation on the Stability of Micelles and on Drug Release", Li, et al.
European Communication, dated Oct. 28, 2011 in co-pending European Patent Application No. EP 05783310.5.
Australian Communication, dated Oct. 28, 2011 in co-pending Australian Patent Application No. 2007252678.
Office Action mailed Apr. 6, 2012 in co-pending U.S. Appl. No. 12/225,230.
Miscellaneous Communication mailed Mar. 19, 2012 in co-pending U.S. Appl. No. 12/312,157.
Office Action mailed Apr. 25, 2012 in co-pending U.S. Appl. No. 12/678,620.
Final Rejection mailed Aug. 21, 2012 in co-pending U.S. Appl. No. 11/662,834.
Notice of Allowance mailed Aug. 28, 2012 in co-pending U.S. Appl. No. 12/225,230.
Notice of Allowance mailed Aug. 7, 2012 in co-pending U.S. Appl. No. 12/312,009.
Office Action-Restriction-mailed Jul. 11, 2012 in co-pending U.S. Appl. No. 12/991,041.
Office Action mailed Aug. 22, 2012 in co-pending U.S. Appl. No. 12/991,041.
Final Rejection mailed Oct. 17, 2012 in co-pending U.S. Appl. No. 12/678,620.
International Search Report and Written Opinion mailed Jan. 24, 2012 in co-pending PCT application No. PCT/JP2011/076373.
Japanese Communication, with partial English translation, mailed May 14, 2013 in co-pending Japanese patent application No. JP 2009-534401.
Japanese Communication, with English translation, mailed Mar. 26, 2013 in co-pending Japanese Patent Application No. 2008-537500.
Chinese Communication, with English translation, mailed Feb. 22, 2013 in co-pending Chinese Patent Application No. 201080021960.6.
Office Action mailed Apr. 18, 2013 in co-pending U.S. Appl. No. 12/311,086.
Final Rejection mailed Mar. 28, 2013 in co-pending U.S. Appl. No. 12/991,041.
Office Action—Restriction—mailed Jan. 29, 2013 in co-pending U.S. Appl. No. 13/319,175.
Advanced Drug Delivery Reviews, vol. 55, No. 2, Feb. 2003, pp. 217-250, "Effective drug delivery by PEGylated drug conjugates", Greenwald, et al.
European Communication mailed May 24, 2013 in corresponding European patent application No. 09722008.1.
Office Action mailed Jun. 12, 2013 in co-pending U.S. Appl. No. 13/319,175.
Canadian Communication issued Jun. 26, 2013 in co-pending Canadian patent application No. CA 2,664,852.
International Preliminary Report on Patentability, with English translation, issued Apr. 7, 2009 and Apr. 22, 2009 in co-pending PCT application No. PCT/JP2007/068841.
Final Rejection mailed Aug. 28, 2013 in co-pending U.S. Appl. No. 12/311,086.
Japanese communication, with English translation, mailed Sep. 24, 2013 in corresponding Japanese patent application No. JP 2010-503871.
Office Action mailed Oct. 7, 2013 in co-pending U.S. Appl. No. 10/548,998.
Final Rejection mailed Jan. 10, 2014 in co-pending U.S. Appl. No. 13/319,175.
Notice of Allowance mailed Jan. 16, 2014 in co-pending U.S. Appl. No. 12/678,620.
Japanese communication, with English translation, mailed Jul. 8, 2014 in corresponding Japanese patent application No. 2010-503871.
Office Action mailed Oct. 1, 2014 in co-pending U.S. Appl. No. 14/241,924.
Chinese communication, with English translation, mailed Jun. 17, 2014 in corresponding Chinese patent application No. 200980110087.5.
International Search Report mailed Dec. 4, 2012 in co-pending PCT application No. PCT/JP2012/072160.
Written Opinion mailed Dec. 4, 2012 in co-pending PCT application No. PCT/JP2012/072160.
International Preliminary Report on Patentability mailed Mar. 20, 2014 in co-pending PCT application No. PCT/JP2012/072160.
Office Action mailed Aug. 25, 2014 in co-pending U.S. Appl. No. 11/662,834.

(56) References Cited

OTHER PUBLICATIONS

Notice of Allowance mailed Sep. 11, 2014 in co-pending U.S. Appl. No. 12/226,962.

Examiner's Answer to Appeal Brief mailed Jul. 29, 2014 in co-pending U.S. Appl. No. 12/311,086.

Notice of Allowance mailed May 15, 2014 in co-pending U.S. Appl. No. 13/319,175 (now US Patent No. 8808749).

Chinese Communication, with English translation, mailed Dec. 31, 2013 in corresponding Chinese patent application No. CN 200980110087.5.

* cited by examiner

HIGH-MOLECULAR WEIGHT CONJUGATE OF PHYSIOLOGICALLY ACTIVE SUBSTANCES

TECHNICAL FIELD

The present invention relates to a high-molecular weight conjugate of physiologically active substances in which a residue of the physiologically active substance having a carboxy group or a residue of the physiologically active substance having an amino group is bonded, through a specific linker, to a carboxy group of a block copolymer having a polyethylene glycol moiety and a polymer moiety having two or more carboxylic acid groups, the use thereof, and a method for manufacturing the same.

BACKGROUND ART

High-molecular weight conjugates obtained by bonding physiologically active substances such as an anticancer agent or an anti-inflammatory agent, especially a physiologically active substances with low solubility in water, to a high-molecular weight carrier have been studied extensively since the high-molecular weight conjugates improve the in vivo pharmacokinetics of the physiologically active substances themselves, the water solubility thereof and the like, and are expected to thus improve the efficacy of the substances as drugs. Particularly block copolymers in which a hydrophilic polymer and a hydrophobic polymer are bonded are characterized by being capable of maintaining the water solubility as the whole polymer even if the amount of a physiologically active substances carried thereon is increased, by forming a micelle having the hydrophobic polymer carrying the physiologically active substances as the inner shell and the hydrophilic polymer covering the surface.

Patent Document 1 discloses a compound in which a drug is bonded to a block copolymer of a polyethylene glycol and a polyaspartic acid and which forms micelles and has water solubility. Patent Document 2 discloses a high-molecular weight derivative of camptothecins in which a side chain carboxy group of a block copolymer of a polyethylene glycol and a polyglutamic acid is bonded to a phenolic hydroxyl group of the camptothecins.

Patent Document 3 discloses a compound in which a drug is bonded to a polyethylene glycol through a specific linker to cause a benzyl elimination reaction. Patent Document 4 discloses a compound in which a drug is bonded to a branched amino acid such as aspartic acid bonded to a polyethylene glycol, through a specific linker to cause a benzyl elimination reaction.

Patent Document 1: Japanese Patent No. 2694923
Patent Document 2: WO 2004/39869
Patent Document 3: Japanese Patent Application Laid-Open Publication (Kohyo) No. 2002-508400
Patent Document 4: Japanese Patent Application Laid-Open Publication (Kohyo) No. 2004-532289

DISCLOSURE OF THE INVENTION

Problems to be Solved by the Invention

In the case of the doxorubicin conjugate disclosed in Patent Document 1, a block copolymer and doxorubicin are directly bonded through an amide bond. However, the amide bond is a chemically stable bonding mode, and therefore the efficacy of such a conjugate is questionable since the in vivo release of the drug by the hydrolysis is very slow. In fact, as a Comparative Example in Examples of the specification of the present application, the antitumor effect was measured when doxorubicin was bonded directly to a block copolymer to find rarely discernible antitumor activity.

In a high-molecular weight derivative of camptothecins disclosed in Patent Document 2, the bonded drugs are sustainably released by selecting drugs having a phenolic hydroxyl group exhibiting a higher hydrolysis reactivity than ordinary phenolic hydroxyl groups and forming an ester of the phenolic hydroxyl group with a carboxylic acid group of polyglutamic acid. However, this method cannot be applied to drugs having an amino group or a carboxy group.

In order to release a drug from a high-molecular weight conjugate disclosed in Patent Document 3, a bond between a polyethylene glycol and a linker needs to be degraded by hydrolyzing enzymes in the body. However, such hydrolyzing enzymes in the body are known to greatly vary not only among species but also among individuals even in the same species, and therefore there is also a concern that the effect of the drug release from the conjugate would be greatly different among individuals when the cleavage of the bond to the drug is dependent on the hydrolyzing enzymes.

A high-molecular weight conjugate disclosed in Patent Document 4 includes aspartic acid as a part of a block copolymer, and a linker is bonded to the aspartic acid. However, the bond between the aspartic acid and the linker of the high-molecular weight conjugate needs to be hydrolyzed by hydrolyzing enzymes in the body as in Patent Document 3, and therefore there is also a concern that release of the drug may vary among species as well as among individuals. The high-molecular weight conjugate disclosed in Patent Document 4 does not form a micelle, and then if the amount of the drug carried on the conjugate is increased, the water solubility may not be maintained.

Means for Solving the Problems

As a result of intensive and extensive studies on a solution for the aforementioned problems, the present inventors have found that a compound in which a residue of a physiologically active substance having a carboxy group or a residue of a physiologically active substance having an amino group is bonded to a side chain carboxy group of a block copolymer having a polyethylene glycol moiety and a polyaspartic acid moiety or a polyglutamic acid moiety through a specific linker to cause a benzyl elimination reaction can release the physiologically active substance under physiological conditions without depending on hydrolyzing enzymes. This finding leads to the completion of the present invention. In the compound, the polyaspartic acid or the polyglutamic acid may presumably form a 5- or 6-membered cyclic imide structure under physiological conditions, whereby an ester bond may be cleaved, and then, the benzyl elimination reaction proceeds to release the physiologically active substance.

Specifically, the present invention relates to the following (1) to (24):

(1) A high-molecular weight conjugate of physiologically active substances, comprising a structure in which a side chain carboxy group of a block copolymer having a polyethylene glycol moiety and a polyaspartic acid moiety or a polyglutamic acid moiety is bonded to a substituent represented by the general formula (I):

$$-Ar-CR^{15}R^{16}-O-C(=O)-A \qquad (I)$$

wherein Ar represents an aromatic hydrocarbon group optionally having a substituent or an aromatic heterocyclic group optionally having a substituent; $R^{15}$ and $R^{16}$ independently represent a hydrogen atom or a (C1 to C6) alkyl group optionally having a substituent; and A represents a residue of the physiologically active substance having a carboxy group or a residue of the physiologically active substance having an amino group.

(2) The high-molecular weight conjugate of physiologically active substances according to (1) above, wherein the physiologically active substances having an amino group are bonded through the amino group.

(3) The high-molecular weight conjugate of physiologically active substances according to (1) or (2) above, represented by the general formula (II):

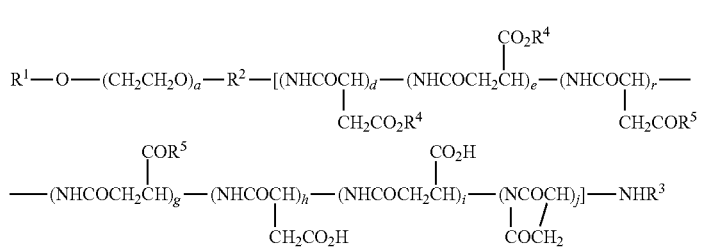

(II)

wherein $R^1$ represents a hydrogen atom or a (C1 to C6) alkyl group; $R^2$ represents a linkage group; $R^3$ represents a hydrogen atom or a (C1 to C6) acyl group; $R^4$ represents a substituent represented by the general formula (III):

—Ar$^1$—CR$^{17}$R$^{18}$—O—C(=O)-A      (III)

wherein Ar$^1$ represents an aromatic hydrocarbon group optionally having a substituent or an aromatic heterocyclic group optionally having a substituent; $R^{17}$ and $R^{18}$ independently represent a hydrogen atom or a (C1 to C6) alkyl group optionally having a substituent; and A represents a residue of the physiologically active substance having a carboxy group or a residue of the physiologically active substance having an amino group; $R^5$ represents a substituent selected from the group consisting of a hydroxymethylphenoxy group optionally having a substituent, a (C1 to C30) alkoxy group, a (C1 to C30) aralkyloxy group, a (C1 to C30) alkylamino group, a di(C1 to C30) alkylamino group, an amino acid with a protected carboxy group, and —NR$^6$CONHR$^7$ wherein $R^6$ and $R^7$, which may be the same or different from each other, represent a (C3 to C6) cyclic alkyl group or a (C1 to C5) alkyl group which may be substituted with a tertiary amino group; a represents an integer of 5 to 11,500; d, e, f, g, h, i and j each represents an integer of 0 to 200; d+e represents an integer of 1 to 200; and d+e+f+g+h+i+j represents an integer of 2 to 200; and respective units of the polyaspartic acid are bonded in any order.

(4) The high-molecular weight conjugate of physiologically active substances according to (3) above, wherein $R^1$ is a (C1 to C3) alkyl group; $R^2$ is a (C2 to C6) alkylene group; $R^3$ is a (C1 to C3) acyl group; Ar$^1$ in the general formula (III) as $R^4$ is a phenyl group in which the bond of Ar$^1$ with a polymer is present in the ortho or para position to the bond with CR$^{17}$R$^{18}$; and a is an integer of 100 to 300; d, e, f, g, h, i and j are each an integer of 0 to 100; d+e is an integer of 1 to 100; and d+e+f+g+h+i+j is an integer of 6 to 100.

(5) The high-molecular weight conjugate of physiologically active substances according to (3) or (4) above, wherein $R^1$ is a methyl group; $R^2$ is a trimethylene group; $R^3$ is an acetyl group; $R^{17}$ and $R^{18}$ in the general formula (III) as $R^4$ are both a hydrogen atom; and $R^5$ is —NR$^6$CONHR$^7$ wherein $R^6$ and $R^7$ are both a cyclohexyl group or an isopropyl group.

(6) The high-molecular weight conjugate of physiologically active substances according to (1) or (2) above, represented by the general formula (IV):

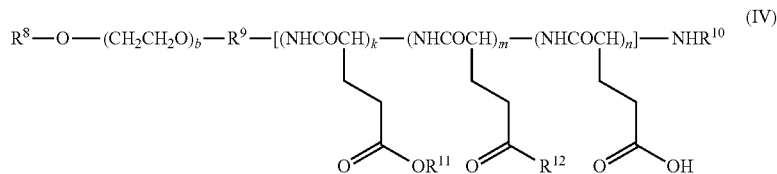

(IV)

wherein $R^8$ represents a hydrogen atom or a (C1 to C6) alkyl group; $R^9$ represents a linkage group; $R^{10}$ represents a hydrogen atom or a (C1 to C6) acyl group; $R^{11}$ represents a substituent represented by the general formula (V):

—Ar$^2$—CR$^{19}$R$^{20}$—O—C(=O)-A      (V)

wherein Ar$^2$ represents an aromatic hydrocarbon group optionally having a substituent or an aromatic heterocyclic group optionally having a substituent; $R^{19}$ and $R^{20}$ each independently represent a hydrogen atom or a (C1 to C6) alkyl group optionally having a substituent; and A represents a residue of the physiologically active substance having a carboxy group or a residue of the physiologically active substance having an amino group; $R^{12}$ represents a substituent selected from the group consisting of a hydroxymethylphenoxy group optionally having a substituent, a (C1 to C30) alkoxy group, a (C1 to C30) aralkyloxy group, a (C1 to C30) alkylamino group, a di(C1 to C30) alkylamino group, an amino acid with a protected carboxy group, and —NR$^{13}$CONHR$^{14}$ wherein $R^{13}$ and $R^{14}$, which may be the same or different from each other, represent a (C3 to C6) cyclic alkyl group or a (C1 to C5) alkyl group which may be substituted with a tertiary amino group; b represents an inte- (7) The high-molecular weight conjugate of physiologically active substances according to (6) above, wherein $R^8$ is a (C1 to C3) alkyl group; $R^9$ is a (C2 to C6) alkylene group; $R^{10}$ is a (C1 to C3) acyl group; $Ar^2$ in the general formula (V) as $R^{11}$ is a phenyl group in which the bond of $Ar^2$ with a polymer is present in the ortho or para position to the bond with $CR^{19}R^{20}$; and b is an integer of 100 to 300; k represents an integer of 1 to 90; m and n each represent an integer of 0 to 90; and k+m+n is an integer of 6 to 90.

(8) The high-molecular weight conjugate of physiologically active substances according to (6) or (7) above, wherein $R^8$ is a methyl group; $R^9$ is a trimethylene group; $R^{10}$ is an acetyl group; $R^{19}$ and $R^{20}$ in the general formula (V) as $R^{11}$ are both a hydrogen atom; and $R^{12}$ is —$NR^{13}CONHR^{14}$ wherein $R^{13}$ and $R^{14}$ are both a cyclohexyl group or an isopropyl group.

(9) A high-molecular weight conjugate of physiologically active substances, obtained by ester-bonding a side chain carboxy group of a block copolymer having a polyethylene glycol moiety and a polyaspartic acid moiety or a polyglutamic acid moiety to a phenolic hydroxyl group of a hydroxybenzyl alcohol derivative, and bonding an alcoholic hydroxyl group of the resultant ester compound to a carboxy group of the physiologically active substance having the carboxy group, or bonding an alcoholic hydroxyl group of the ester compound to an amino group of the physiologically active substance having the amino group through a carbonyl group.

(10) The high-molecular weight conjugate of physiologically active substances according to any one of (1) to (9) above, wherein the physiologically active substance is an anticancer agent.

(11) The high-molecular weight conjugate of physiologically active substances according to any one of (1) to (9) above, wherein the physiologically active substance having an amino group is an anthracycline-based anticancer agent.

(12) The high-molecular weight conjugate of physiologically active substances according to (11) above, wherein the anthracycline-based anticancer agent is doxorubicin, daunorubicin, epirubicin, pirarubicin or amrubicin.

(13) The high-molecular conjugate of physiologically active substances according to any one of (1) to (9) above, wherein the physiologically active substance is a physiologically active peptide.

(14) The high-molecular conjugate of physiologically active substances according to (13) above, wherein the physiologically active peptide is bestatin or a derivative thereof.

(15) The high-molecular conjugate of physiologically active substances according to any one of (1) to (9) above, wherein the physiologically active substance is an anti-inflammatory agent.

(16) The high-molecular conjugate of physiologically active substances according to any one of (1) to (9) above, wherein the physiologically active substance having a carboxy group is indomethacin, etodolac or a derivative thereof.

(17) The high-molecular conjugate of physiologically active substances according to any one of (1) to (16) above, wherein the high-molecular weight forms a micelle in water.

(18) A pharmaceutical product comprising a high-molecular conjugate of physiologically active substances according to any one of (1) to (17) above as an active ingredient.

(19) An anticancer agent comprising a high-molecular conjugate of physiologically active substances according to any one of (10) to (12) above as an active ingredient.

(20) An anti-inflammatory agent comprising a high-molecular conjugate of physiologically active substances according to (15) above as an active ingredient.

(21) A method for manufacturing a high-molecular conjugate of physiologically active substances according to (1) or (2) above, the method comprising ester-bonding a side chain carboxy group of a block copolymer having a polyethylene glycol moiety and a polyaspartic acid moiety or a polyglutamic acid moiety to a phenolic hydroxyl group of a hydroxybenzyl alcohol compound, and bonding an alcoholic hydroxyl group of the ester compound to a carboxy group of the physiologically active substance having the carboxy group, or bonding an alcoholic hydroxyl group of the ester compound to an amino group of the physiologically active substance having the amino group through a carbonyl group.

(22) A compound comprising a structure in which a side chain carboxy group of a block copolymer having a polyethylene glycol moiety and a polyaspartic acid moiety or a polyglutamic acid moiety is bonded to a substituent represented by the general formula (VI):

$$-Ar-CR^{15}R^{16}-OH \qquad (VI)$$

wherein Ar represents an aromatic hydrocarbon group optionally having a substituent or an aromatic heterocyclic group optionally having a substituent; and $R^{15}$ and $R^{16}$ independently represent a hydrogen atom or a (C1 to C6) alkyl group optionally having a substituent.

(23) A compound represented by the general formula (II):

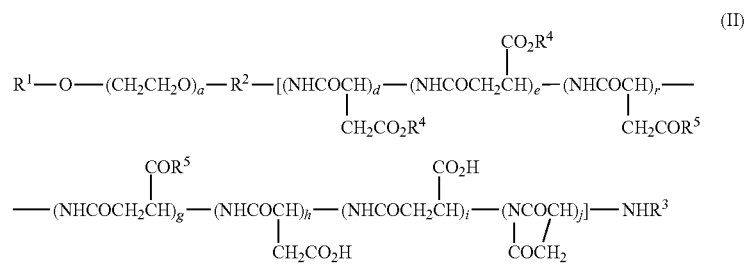

wherein $R^1$ represents a hydrogen atom or a (C1 to C6) alkyl group; $R^2$ represents a linkage group; $R^3$ represents a hydrogen atom or a (C1 to C6) acyl group; $R^4$ represents a substituent represented by the general formula (VII):

$$-Ar^1-CR^{17}R^{18}-OH \quad (VII)$$

wherein $Ar^1$ represents an aromatic hydrocarbon group optionally a substituent or an aromatic heterocyclic group optionally having a substituent; $R^{17}$ and $R^{18}$ independently represent a hydrogen atom or a (C1 to C6) alkyl group optionally having a substituent; $R^5$ represents a substituent selected from the group consisting of a hydroxymethylphenoxy group optionally having a substituent, a (C1 to C30) alkoxy group, a (C1 to C30) aralkyloxy group, a (C1 to C30) alkylamino group, a di(C1 to C30) alkylamino group, an amino acid with a protected carboxy group, and $-NR^6CONHR^7$ wherein $R^6$ and $R^7$, which may be the same or different from each other, represent a (C3 to C6) cyclic alkyl group or a (C1 to C5) alkyl group which may be substituted with a tertiary amino group; a represents an integer of 5 to 11,500; d, e, f, g, h, i and j each represent an integer of 0 to 200; d+e represents an integer of 1 to 200; and d+e+f+g+h+i+j represents an integer of 2 to 200; and the respective units of the polyaspartic acid are bonded in any order.

(24) A compound represented by the general formula (IV):

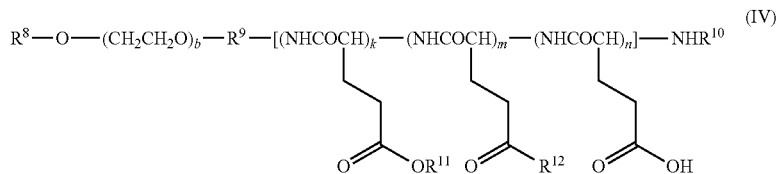

wherein $R^8$ represents a hydrogen atom or a (C1 to C6) alkyl group; $R^9$ represents a linkage group; $R^{10}$ represents a hydrogen atom or a (C1 to C6) acyl group; $R^{11}$ represents a substituent represented by the general formula (VIII):

$$-Ar^2-CR^{19}R^{20}-OH \quad (VIII)$$

wherein $Ar^2$ represents an aromatic hydrocarbon group optionally having a substituent or an aromatic heterocyclic group optionally having a substituent; and $R^{19}$ and $R^{20}$ independently represent a hydrogen atom or a (C1 to C6) alkyl group optionally having a substituent; $R^{12}$ represents a substituent selected from the group consisting of a hydroxymethylphenoxy group optionally having a substituent, a (C1 to C30) alkoxy group, a (C1 to C30) aralkyloxy group, a (C1 to C30) alkylamino group, a di(C1 to C30) alkylamino group, an amino acid with a protected carboxy group, and $-NR^{13}CONHR^{14}$ wherein $R^{13}$ and $R^{14}$, which may be the same or different from each other, represent a (C3 to C6) cyclic alkyl group or a (C1 to C5) alkyl group which may be substituted with a tertiary amino group; b represents an integer of 5 to 11,500; k represents an integer of 1 to 200; m and n each represent an integer of 0 to 200; and k+m+n represents an integer of 2 to 200; and the respective units of the polyglutamic acid are bonded in any order.

Effects of the Invention

The high-molecular weight conjugate of physiologically active substances according to the present invention is a compound in which a residue of the physiologically active substance having a carboxy group or a residue of the physiologically active substance having an amino group is bonded to a side chain carboxy group of a block copolymer having a polyethylene glycol moiety and a polyaspartic acid moiety or a polyglutamic acid moiety through a specific linker to cause a benzyl elimination reaction. As being capable of releasing the physiologically active substance under physiological conditions without depending on hydrolyzing enzymes in the body, the high-molecular weight conjugate of the present invention is expected to achieve efficacious therapeutic effects of the physiologically active substance without being affected by differences among individuals. Furthermore, the release rate can be regulated suitably by using polyaspartic acid or polyglutamic acid which can be selected in accordance with the physiologically active substances.

BEST MODE FOR CARRYING OUT THE INVENTION

In the high-molecular weight conjugate of physiologically active substances according to the present invention, a side chain carboxy group of a block copolymer having a polyethylene glycol moiety and a polyaspartic acid moiety or a polyglutamic acid moiety is bonded to a substituent represented by the general formula (I):

$$-Ar-CR^{15}R^{16}-O-C(=O)-A \quad (I)$$

wherein Ar represents an aromatic hydrocarbon group optionally having a substituent or an aromatic heterocyclic group optionally having a substituent; $R^{15}$ and $R^{16}$ independently represent a hydrogen atom or a (C1 to C6) alkyl group optionally having a substituent; and A represents a residue of the physiologically active substance having a carboxy group or a residue of the physiologically active substance having an amino group.

The block copolymer having a polyethylene glycol moiety and a polyaspartic acid moiety or a polyglutamic acid moiety in the high-molecular weight conjugate of physiologically active substances according to the present invention is preferably formed by bonding a polyethylene glycol moiety to a polymer in which aspartic acid or glutamic acid or a derivative thereof forms a polymer backbone through amido bonds and which has carboxy groups in the side chain.

In the general formula (I), Ar includes aromatic hydrocarbon groups optionally having a substituent, or aromatic heterocyclic groups optionally having a substituent, and the substituents include a (C1 to C6) alkyl group, a (C1 to C6) alkoxy group, a nitro group and a halogen atom, and examples thereof include a methyl group, an ethyl group, a tert-butyl group, a methoxy group and a bromine atom. The number of substituents and the substitution positions of the substituents are not particularly limited.

Above all, examples of —Ar— include the following groups.

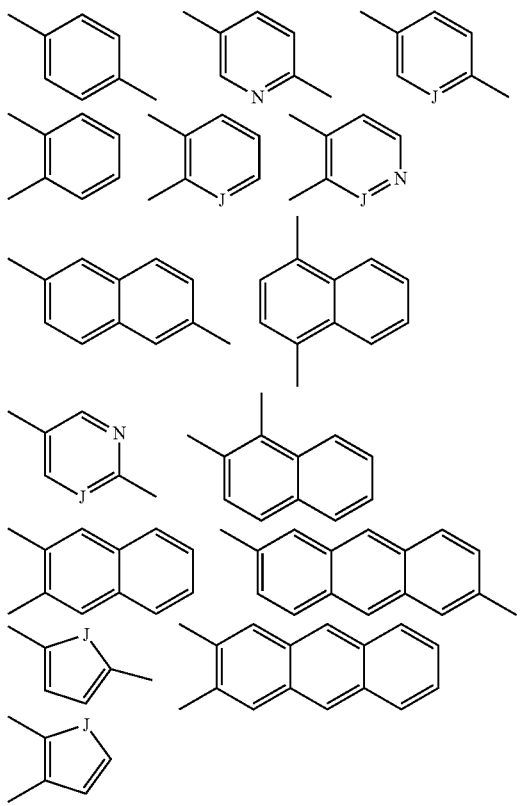

wherein N represents a nitrogen atom; and J represents an oxygen atom or a sulfur atom.

Particularly, the following groups which are unsubstituted phenyl groups are preferred.

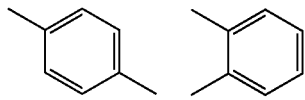

In the general formula (I), $R^{15}$ and $R^{16}$ independently include a hydrogen atom or a (C1-C6) alkyl group optionally having a substituent, and examples of "the (C1-C6) alkyl group optionally having a substituent" include a methyl group, an ethyl group, an n-propyl group, an isopropyl group, an n-butyl group, an s-butyl group, an isobutyl group, an n-pentyl group and an n-hexyl group. Examples of substituents in "the (C1-C6) alkyl group optionally having a substituent" include an amino group, a methylamino group, a dimethylamino group, an ethylamino group and a diethylamino group. Preferably, $R^{15}$ and $R^{16}$ are both a hydrogen atom.

In the general formula (I), AH (H is a hydrogen atom) refers to a physiologically active substance having an amino group and is not particularly limited. However, in a preferable high-molecular weight conjugate, an amino group of the physiologically active substance having the amino group is bonded through a carbonyl group to an alcoholic hydroxyl group of a hydroxybenzyl alcohol compound which is bonded to a side chain carboxy group of a block copolymer having a polyethylene glycol moiety and a polyaspartic acid moiety or a polyglutamic acid moiety. Therefore the physiologically active substance is preferably a physiologically active substance having a primary or secondary amino group.

Examples of the physiologically active substance having an amino group include anthracycline-based anticancer agents and cytidine-based anticancer agents. Particularly preferred are doxorubicin, daunorubicin, epirubicin, pirarubicin, amrubicin, ethynyl cytidine, CNDAC (2'-cyano-2'-deoxy-1-β-D-arabinofuranosyl cytosine), gemcitabine and the like.

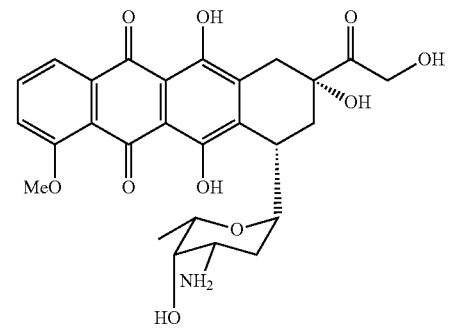

Doxorubicin

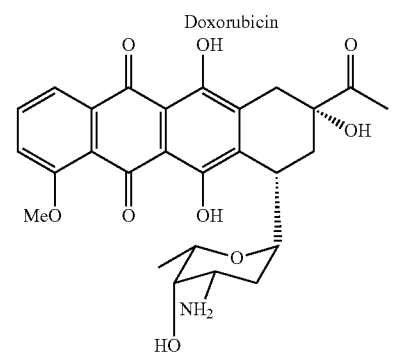

Daunorubicin

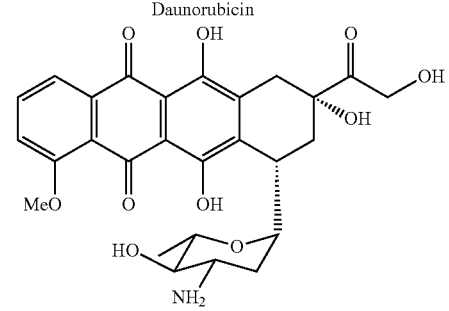

Epirubicin

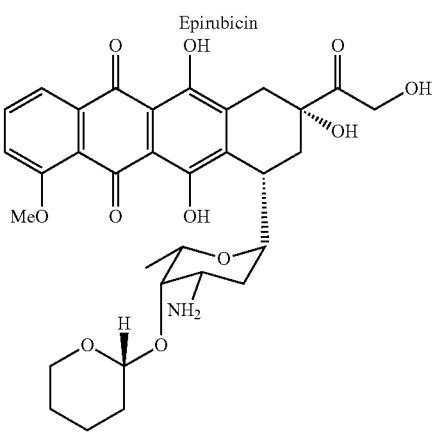

Pirarubicin

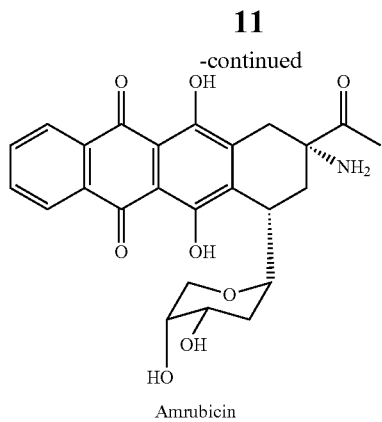

Amrubicin

The physiologically active substance in the general formula (I) may be physiologically active peptides. Using an amino group or a carboxy group at the terminals of the peptides or at other positions in the peptides, high-molecular weight conjugates carrying the peptides can be prepared. Despite their useful physiological activity in vitro, many of the peptides may not exhibit the effects in vivo because they may rapidly be degraded by hydrolyzing enzymes or other enzymes in vivo. Such peptides are expected to exhibit their effects even in vivo by being incorporated into the high-molecular weight conjugate according to the present invention.

Examples of the peptides include bestatin and bestatin methyl ester shown below, and Glufanide, Ghrelin, Tertomotide, PR1, Octreotide, Lanreotide and Pasireotide.

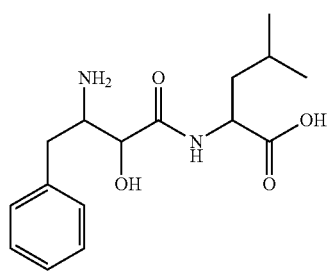

Bestatin

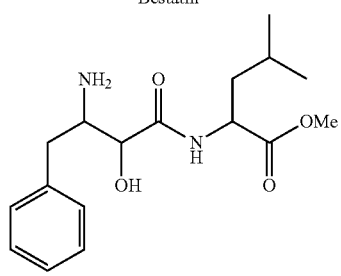

Bestatin methyl ester

In the general formula (I), the residue of a physiologically active substance having a carboxy group as A means that the formula "HO—C(=O)-A" represents the physiologically active substance. The physiologically active substance includes, but is not particularly limited to, nonsteroidal anti-inflammatory agents and anticancer agents, such as, for example, indomethacin, etodolac, mefenamic acid, diclofenac, flurbiprofen, ibuprofen, methotrexate and DMXAA.

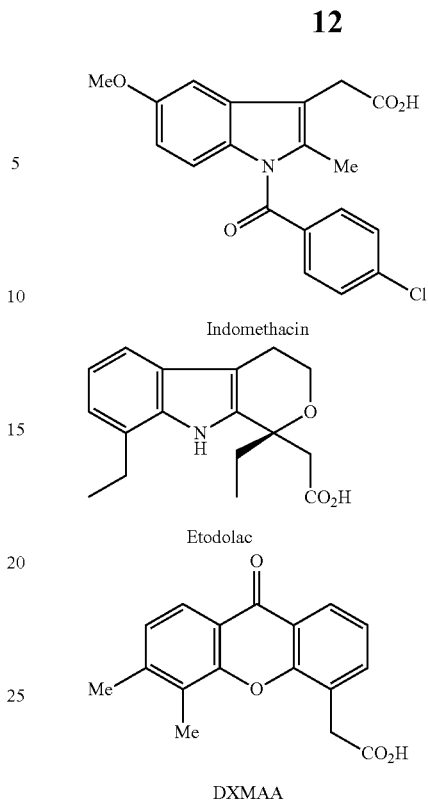

Indomethacin

Etodolac

DXMAA

The high-molecular weight conjugate of physiologically active substances according to the present invention is preferably a compound represented by the aforementioned general formula (II), wherein $R^1$ represents a hydrogen atom or a (C1 to C6) alkyl group; $R^2$ represents a linkage group; $R^3$ represents a hydrogen atom or a (C1 to C6) acyl group; $R^4$ represents a substituent represented by the general formula (III):

$$-Ar^1-CR^{17}R^{18}-O-C(=O)-A \quad (III)$$

wherein $Ar^1$ represents an aromatic hydrocarbon group optionally having a substituent or an aromatic heterocyclic group optionally having a substituent; $R^{17}$ and $R^{18}$ independently represent a hydrogen atom or a (C1 to C6) alkyl group optionally having a substituent; and A represents a residue of the physiologically active substance having a carboxy group or a residue of the physiologically active substance having an amino group; $R^5$ represents a substituent selected from the group consisting of a hydroxymethylphenoxy group optionally having a substituent, a (C1 to C30) alkoxy group, a (C1 to C30) aralkyloxy group, a (C1 to C30) alkylamino group, a di(C1 to C30) alkylamino group, an amino acid with a protected carboxy group, and —$NR^6CONHR^7$ wherein $R^6$ and $R^7$, which may be the same or different from each other, represent a (C3 to C6) cyclic alkyl group or a (C1 to C5) alkyl group which may be substituted with a tertiary amino group; and a represents an integer of 5 to 11,500; d, e, f, g, h, i and j each represent an integer of 0 to 200; d+e represents an integer of 1 to 200; and d+e+f+g+h+i+j represents an integer of 2 to 200.

The (C1 to C6) alkyl group in $R^1$ in the general formula (II) includes (C1 to C6) straight chain or branched alkyl groups, and preferred are (C1 to C4) alkyl groups, including, for example, a methyl group, an ethyl group, an n-propyl group and an n-butyl group. Particularly preferred is a methyl group.

The linkage group as $R^2$ in the general formula (II) is preferably a (C2 to C6) alkylene group, including, for example, an ethylene group, a trimethylene group and a tetramethylene group. A trimethylene group is particularly preferred.

The (C1 to C6) acyl group as $R^3$ in the general formula (II), not particularly limited, preferably includes (C1 to C3) acyl groups, including a formyl group, an acetyl group and an n-propionyl group. An acetyl group is particularly preferred.

The $Ar^1$ in the general formula (III) as $R^4$ in the general formula (II) includes the same groups as Ar in the aforementioned general formula (I), and preferable groups thereof are also the same.

The $R^{17}$ and $R^{18}$ in the general formula (III) as $R^4$ in the general formula (II) include the same groups as the $R^{15}$ and $R^{16}$ in the aforementioned general formula (I), and preferable groups thereof are similarly a hydrogen atom.

The group A in the general formula (III) as $R^4$ in the general formula (II) includes the same compounds as A in the aforementioned general formula (I), and preferable compounds thereof are also the same.

The $R^5$ in the general formula (II) represents a group selected from the group consisting of a hydroxymethylphenoxy group optionally having a substituent, a (C1 to C30) alkoxy group, a (C1 to C30) aralkyloxy group, a (C1 to C30) alkylamino group, a di(C1 to C30) alkylamino group, an amino acid with a protected carboxy group, and —$NR^6CONHR^7$ wherein $R^6$ and $R^7$, which may be the same or different from each other, represent a (C3 to C6) cyclic alkyl group or a (C1 to C5) alkyl group which may be substituted with a tertiary amino group. The groups selected as $R^5$ in the general formula (II) may be the same or different in one molecule, and a block copolymer used in the high-molecular weight conjugate according to the present invention may include a single-type R5 or may exist as a mixture of compounds having different substituents as $R^5$ in each molecule.

Examples of the hydroxymethylphenoxy group which optionally having a substituent include a 4-hydroxymethylphenoxy group, a 2-hydroxymethylphenoxy group, a 4-hydroxymethyl-2-methoxyphenoxy group, a 4-hydroxymethyl-2,6-dimethoxyphenoxy group, a 4-hydroxymethyl-2,6-di-tert-butylphenoxy group, a 2-hydroxymethyl-4-nitrophenoxy group, a 2-hydroxymethyl-6-methoxyphenoxy group and a 2-hydroxymethyl-4-bromophenoxy group. A 4-hydroxymethylphenoxy group, and a 2-hydroxymethylphenoxy group are preferred.

The (C1 to C30) alkoxy group includes straight-chain or branched (C1 to C30) alkoxy groups, and preferred is a straight-chain or branched (C1 to C10) alkoxy group, including a methoxy group, an ethoxy group, an n-propoxy group, an i-propoxy group, an n-butoxy group and a t-butoxy group. Examples of the (C1 to C30) aralkyloxy group include straight-chain or branched (C1 to C30) aralkyloxy groups, and preferred is a straight-chain or branched (C1 to C12) aralkyloxy groups, including a 4-phenylbutoxy group.

Examples of the (C1 to C30) alkylamino group or the di(C1 to C30) alkylamino group include straight-chain or branched (C1 to C30) alkylamino groups or a straight-chain or branched di(C1 to C30) alkylamino groups, and preferred is a straight-chain or branched (C1 to C20) alkylamino group or straight-chain or branched di(C1 to C20) alkylamino groups, including a methylamino group, an ethylamino group, an n-propylamino group, an i-propylamino group, an n-butylamino group, a t-butylamino group, a dimethylamino group, a diethylamino group and a di(n-butyl) amino group.

Examples of the amino acid with a protected carboxy group include an amino acid generally used in peptide synthesis, in which a carboxyl group is protected, including, for example, a phenylalanine benzyl ester.

Examples of the group —$NR^6CONHR^7$ as $R^5$ in the general formula (II) wherein $R^6$ and $R^7$, which may be the same or different, represent a (C3 to C6) cyclic alkyl group or a (C1 to C5) alkyl group which may be substituted with a tertiary amino group, include, but are not particularly limited to, for example a cyclohexylaminocarbonyl-cyclohexylamino group and an isopropylaminocarbonyl-isopropylamino group.

The polyaspartic acid moiety in the high-molecular weight conjugate of physiologically active substances represented by the aforementioned general formula (II) according to the present invention includes constituting units of α-amino acid type, β-amino acid type and cyclized type. These constituting units may be bonded in any order without any particular limitation, and each type of the amino acids may be bonded to form a block-type form or a random-type form.

The total number of aspartic acid in the polyaspartic acid moiety in the high-molecular weight conjugate of physiologically active substances represented by the aforementioned general formula (II) is represented by "d+e+f+g+h+i+j". The total number of aspartic acids may be determined, for example, based on the amount of aspartic acid derivatives used in the preparation of the block copolymer and is about 2 to 200, preferably about 6 to 100, more preferably about 15 to 90.

The proportion of the number of aspartic acid residues bonded to the physiologically active substance (d+e) based on the total number of aspartic acid (d+e+f+g+h+i+j) is 1 to 100%, preferably 1 to 90%, more preferably 2 to 60%. In addition, the number of aspartic acid residues (d+e) is about 1 to 200, preferably about 1 to 100, more preferably about 1 to 90.

The proportion of the α-amino acid type (d+f+h) based on the total number of aspartic acid residues (d+e+f+g+h+i+j) is 10 to 100%, preferably 20 to 100%. The proportion of the β-amino acid type (e+g+i) is 0 to 90%, preferably 0 to 80%. The proportions can appropriately be changed, for example, by suitably selecting a deprotection condition for a protecting group in the polyaspartic acid.

The molecular weight of the polyethylene glycol moiety in the aforementioned general formula (II) is about 300 to 500,000, preferably about 500 to 100,000, more preferably about 1,000 to 50,000. "a" in the aforementioned general formula (II) is an integer of about 5 to 11,500, preferably an integer of about 8 to 2,300, more preferably an integer of about 100 to 300.

Also preferred as the high-molecular weight conjugate of physiologically active substances according to the present invention is a compound represented by the aforementioned general formula (IV) wherein $R^8$ represents a hydrogen atom or a (C1 to C6) alkyl group;

$R^9$ represents a linkage group; $R^{10}$ represents a hydrogen atom or a (C1 to C6) acyl group;

$R^{11}$ represents a substituent represented by the general formula (V):

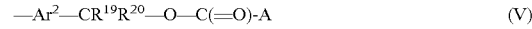

$$—Ar^2—CR^{19}R^{20}—O—C(=O)\text{-}A \qquad (V)$$

wherein $Ar^2$ represents an aromatic hydrocarbon group optionally having a substituent or an aromatic heterocyclic group optionally having a substituent; $R^{19}$ and $R^{20}$ independently represent a hydrogen atom or a (C1 to C6) alkyl group optionally a substituent; and A represents a residue of the physiologically active substance having a carboxy group or a residue of the physiologically active substance having an amino group;

$R^{12}$ represents a substituent selected from the group consisting of a hydroxymethylphenoxy group optionally having a substituent, a (C1 to C30) alkoxy group, a (C1 to C30) aralkyloxy group, a (C1 to C30) alkylamino group, a di(C1 to C30) alkylamino group, an amino acid with a protected carboxy group, and —NR$^{13}$CONHR$^{14}$ wherein R$^{13}$ and R$^{14}$, which may be the same or different from each other, represent a (C3 to C6) cyclic alkyl group or a (C1 to C5) alkyl group which may be substituted with a tertiary amino group; and b represents an integer of 5 to 11,500; k represents an integer of 1 to 200; m and n each represent an integer of 0 to 200, and k+m+n represents an integer of 2 to 200.

The (C1 to C6) alkyl group as R$^8$ in the general formula (IV) includes the same groups as in R$^1$ in the aforementioned general formula (II), and preferable groups thereof are the same, and a methyl group is particularly preferred.

The linkage group as R$^9$ in the general formula (IV) is preferably a (C2 to C6) alkylene group, and examples thereof include an ethylene group, a trimethylene group and a tetramethylene group. Above all, a trimethylene group is particularly preferred.

The (C1 to C6) acyl group as R$^{10}$ in the general formula (IV) includes the same groups as in R$^3$ in the aforementioned general formula (II), and preferable groups thereof are the same, and an acetyl group is particularly preferred.

Ar$^2$ in the general formula (V) as R$^{11}$ in the general formula (IV) includes the same groups as Ar in the aforementioned general formula (I), and preferable groups thereof are the same.

The R$^{19}$ and R$^{20}$ in the general formula (V) as R$^{11}$ in the general formula (IV) include the same groups as R$^{15}$ and R$^{16}$ in the aforementioned general formula (I), and a preferable group thereof is similarly a hydrogen atom.

"A" in the general formula (V) as R$^{11}$ in the general formula (IV) includes the same compounds as A in the aforementioned general formula (I), and preferable compounds thereof are also the same.

The R$^{12}$ in the general formula (IV) represents a group selected from the group consisting of a hydroxymethylphenoxy group optionally having a substituent, a (C1 to C30) alkoxy group, a (C1 to C30) aralkyloxy group, a (C1 to C30) alkylamino group, a di(C1 to C30) alkylamino group, an amino acid with a protected carboxy group, and —NR$^{13}$CONHR$^{14}$ wherein R$^{13}$ and R$^{14}$, which may be the same or different from each other, represent a (C3 to C6) cyclic alkyl group or a (C1 to C5) alkyl group which may be substituted with a tertiary amino group. The groups selected as R$^{12}$ in the general formula (IV) may be the same or different in one molecule, and a block copolymer used in the high-molecular weight conjugate according to the present invention may include a single-type R$^{12}$ or may exist as a mixture of compounds having different substituents as R$^{12}$ in each molecule.

The hydroxymethylphenoxy group optionally having a substituent includes the same groups as the hydroxymethylphenoxy group which may have a substituent in R$^5$ in the aforementioned general formula (II), and preferable groups thereof are the same.

The (C1 to C30) alkoxy group, the (C1 to C30) aralkyloxy group, the (C1 to C30) alkylamino group and the di(C1 to C30) alkylamino group as R$^{12}$ in the general formula (IV) include the same groups as the (C1 to C30) alkoxy group, the (C1 to C30) aralkyloxy group, the (C1 to C30) alkylamino group and the di(C1 to C30) alkylamino group as R$^5$ in the aforementioned general formula (II).

The amino acid with a protected carboxy group for R$^{12}$ in the general formula (IV) includes amino acids having a carboxy group protected, used in the common peptide synthesis, and examples thereof include phenylalanine benzyl ester.

The group —NR$^{13}$CONHR$^{14}$ wherein R$^{13}$ and R$^{14}$, which may be the same or different from each other, represent a (C3 to C6) cyclic alkyl group or a (C1 to C5) alkyl group which may be substituted with a tertiary amino group, for R$^{12}$ in the general formula (IV) includes the same groups as the —NR$^6$CONHR$^7$ as R$^5$ in the general formula (II), and preferable groups thereof are also the same.

The total number of glutamic acid residues of the polyglutamic acid moiety in the high-molecular weight conjugate of physiologically active substances represented by the aforementioned general formula (IV) according to the present invention is represented by k+m+n and is about 2 to 200, preferably about 6 to 90, more preferably 6 to 60.

The proportion of the number of glutamic acid residues (k) to which the physiologically active substance is bonded on the basis of the total number of glutamic acid residues (k+m+n) is 1 to 100%, preferably 3 to 90%, more preferably 4 to 60%. The number of glutamic acid residues (k) is 1 to 200, preferably about 1 to 90, more preferably about 2 to 30.

Each constituting units of the glutamic acid moiety in the high-molecular weight conjugate of physiologically active substances represented by the aforementioned general formula (IV) may be bonded in any order, and amino acids of each type may be bonded to form a block-type form or a random-type form.

"b" in the aforementioned general formula (IV) is an integer of about 5 to 11,500, preferably an integer of about 8 to 2,300, more preferably an integer of about 100 to 300.

The molecular weight of the polyethylene glycol moiety in the aforementioned general formula (IV) is about 300 to 500,000, preferably about 500 to 100,000, more preferably about 1,000 to 50,000.

The molecular weight of the high-molecular weight conjugate of physiologically active substances according to the present invention is about 500 to 600,000, preferably about 600 to 110,000, more preferably about 1,100 to 80,000. According to the present invention, the term "molecular weight" refers to a weight average molecular weight determined by the GPC method.

The high-molecular weight conjugate of physiologically active substances according to the present invention may form a micelle having a polyethylene glycol moiety as the outer shell in water.

The high-molecular weight conjugate of physiologically active substances according to the present invention is obtained by ester-bonding a side chain carboxy group of a block copolymer having a polyethylene glycol moiety and a polyaspartic acid moiety or a polyglutamic acid moiety to a phenolic hydroxyl group of a hydroxybenzyl alcohol compound having an alcoholic hydroxyl group protected by using a dehydrating condensation agent in an organic solvent to form an ester compound, and deprotecting the protecting group, and then, bonding the alcoholic hydroxyl group of the ester compound to a carboxy group of the physiologically active substance having the carboxy group or bonding the alcoholic hydroxyl group of the ester compound to an amino group of the physiologically active substance having the amino group through a carbonyl group. The manufacturing method of the high-molecular weight conjugate according to the present invention is also included in the present invention. An intermediate to which the hydroxybenzyl alcohol compound is bonded is also included in the present invention.

That is, the high-molecular weight conjugate of the present invention is obtained by a method described below. For example, a block copolymer of a polyethylene glycol moiety and a polyaspartic acid prepared according to the method disclosed in Japanese Patent No. 3268913 and a hydroxybenzyl alcohol compound in which an alcoholic hydroxyl group and functional groups other than phenolic hydroxyl groups are protected as necessary are subjected to a reaction using a dehydrating condensation agent such as dicyclohexylcarbodiimide (DCC), diisopropylcarbodiimide (DIPC), 1-ethyl-3-(3-dimethylaminopropyl)carbodiimide hydrochloride salt (WSC) and 1-ethoxycarbonyl-2-ethoxy-1,2-dihydroxyquinolinone (EEDQ) at a temperature of 0 to 180° C., preferably 5 to 50° C. in an organic solvent in which both of the block copolymer and the hydroxybenzyl alcohol compound are dissolved, preferably in an aprotic polar solvent such as N,N-dimethylformamide (DMF), 1,3-dimethyl-2-imidazolidinone (DMI) and N-methylpyrrolidone (NMP). In the case where a physiologically active substance having a carboxy group is bonded thereafter, the protecting group of the alcoholic hydroxyl group at the benzyl-position is deprotected, and then, the alcoholic hydroxyl group at the benzyl-position is ester-bonded to the carboxy group of the physiologically active substance in which functional groups other than the carboxy group have been protected as necessary by using the aforementioned dehydrating condensation agent in the aforementioned solvent, and the protecting groups are deprotected as necessary. In the case where a physiologically active substance having an amino group is bonded, the protecting group of the alcoholic hydroxyl group at the benzyl-position is deprotected, and thereafter, the alcoholic hydroxyl group at the benzyl-position is condensed through a carbonyl group with the amino group of the physiologically active substance in which functional groups other than the amino group have been protected as necessary by using disuccinyl carbonate, carbonyldiimidazole or the like in the aforementioned solvent at 0 to 30° C., and the protecting groups are deprotected as necessary.

In the manufacturing method of the present invention, for example, a block copolymer of a polyethylene glycol moiety and a polyglutamic acid prepared by the method according to Japanese Patent Laid-Open (Kokai) No. 5-955 may be used in place of the aforementioned block copolymer of a polyethylene glycol moiety and a polyaspartic acid.

In the condensation reaction, a reaction aid such as N,N-dimethylaminopyridine (DMAP) may be used.

In addition, a high-molecular weight conjugate of physiologically active substances in which $R^5$ in the general formula (II) is the group —$NR^6CONHR^7$ wherein $R^6$ and $R^7$, which may be the same or different from each other, represent a (C3 to C6) cyclic alkyl group or a (C1 to C5) alkyl group which may be substituted with a tertiary amino group, or a high-molecular weight conjugate of a physiologically active substance in which $R^{12}$ in the general formula (IV) is the group —$NR^{13}CONHR^{14}$ wherein $R^{13}$ and $R^{14}$, which may be the same or different from each other, represent a (C3 to C6) cyclic alkyl group or a (C1 to C5) alkyl group which may be substituted with a tertiary amino group may also be obtained by a reaction using the aforementioned carbodiimides as a condensation agent.

As a method for manufacturing a compound represented by the general formula (II) or (IV) in which $R^5$ or $R^{12}$ in the compound is a (C1 to C30) alkoxy group, a (C1 to C30) aralkyloxy group, a (C1 to C30) alkylamino group, a di(C1 to C30) alkylamino group or an amino acid with a protected carboxy group, there can be mentioned a method in which a carboxy group of the block copolymer is first activated by a method used in an ordinary condensation reaction, and then reacted with a corresponding alcohol, a corresponding amine, a corresponding amino acid with a protected carboxy group in an amount to be introduced under basic conditions; and a method in which a corresponding alcohol, a corresponding amine, a corresponding amino acid with a protected carboxy group is first activated by a method used in an ordinary condensation reaction, and is then reacted with a polymer.

It is also possible to re-activate any unreacted carboxy groups remained after the bonding of the hydroxybenzyl alcohol compound in a similar reaction, and then to introduce into the re-activated carboxy groups a (C1 to C30) alkoxy group, a (C1 to C30) aralkyloxy group, a (C1 to C30) alkylamino group, a di(C1 to C30) alkylamino group, an amino acid with a protected carboxy group. Alternatively, different alcohols, amines and the like may be repeatedly reacted to synthesize a mixture of compounds having various substituents as the $R^5$ or the $R^{12}$, with which the hydroxybenzyl alcohol compound may subsequently be condensed.

However, the method for manufacturing the high-molecular weight conjugate of physiologically active substances according to the present invention is not limited to the aforementioned methods.

The high-molecular weight conjugate of physiologically active substances according to the present invention can be used as a pharmaceutical product which is indicated for a disease for which the physiologically active substance carried on the conjugate have an efficacy. Examples of the pharmaceutical products include anticancer agents and anti-inflammatory agents. The high-molecular weight conjugate according to the present invention can be used in a dosage form which is conventionally used, including injections, tablets, and powders. For formulation process, pharmaceutically acceptable carriers which are conventionally used, for example, binding agents, lubricating agents, disintegrating agents, solvents, vehicles, solubilizing agents, dispersing agents, stabilizing agents, suspending agents, preservatives, soothing agents, colorants and flavors can also be used.

The high-molecular weight conjugate of physiologically active substances according to the present invention is used preferably as an injection, and usually water, a physiological saline, a 5% glucose or mannitol liquid, a water-soluble organic solvent (for example, glycerol, ethanol, dimethylsulfoxide, N-methylpyrrolidone, polyethylene glycol, cremophor, and a mixture thereof) or a mixture of water and the water-soluble organic solvents can be used.

The dosage of the high-molecular weight conjugate of physiologically active substances according to the present invention can vary as a matter of course, depending on the physiologically active substance as well as the sexuality, ages, physiological conditions, pathological conditions and the like of patients. The conjugate is parenterally administered, typically at a dose of 0.01 to 500 mg/m$^2$, preferably 0.1 to 250 mg/m$^2$, as an active ingredient per day in an adult. The administration by injection is performed intravenously, intraarterially, or into an affected site (a tumor site, an inflammation site, and the like), for example.

EXAMPLES

Hereinafter, the present invention will be illustrated more specifically with reference to Examples. However, the scope of the present invention is not limited to these Examples.

The Gaussian distribution analysis was conducted using a ZetaPotential/Particlesizer NICOMP 380ZLS (manufactured by Particle Sizing Systems Co.).

Example 1

Synthesis of Compound 1 (a phenyl ester conjugate of a block copolymer consisting of a methoxypolyethylene glycol moiety having a molecular weight of 5,000 and a polyaspartic acid moiety having a polymerization number of 30 and 4-(hydroxymethyl)phenol: in the general formula (II), $R^1$=Me (a methyl group), $R^2$=a trimethylene group, $R^2$=Ac (an acetyl group), $R^4$=4-(hydroxymethyl)phenoxy group, $R^5$=an isopropylaminocarbonylisopropylamino group, and d+e+f+g+h+i+j=30, and a=113)

A methoxypolyethylene glycol-polyaspartic acid block copolymer (a polymerization number of aspartic acid: 30, 1.0 g) prepared by the method according to Japanese Patent No. 3268913, and 4-(tert-butyldimethylsilanyloxymethyl)-phenol (847 mg) prepared by the method according to Patent Document 4 were dissolved in DMF (8 ml), and DMAP (43 mg) and DIPC (1.11 ml) were added at 15° C. The mixture was stirred for 20 hours. To the reaction solution, ethanol (12 ml), ethyl acetate (12 ml) and diisopropyl ether (96 ml) were added, the mixture was stirred at room temperature for 2 hours, and thereafter, a precipitate was collected by filtration and washed with ethanol/diisopropyl ether (1/4 (v/v), 10 ml). The resultant precipitate was dissolved in acetonitrile (15 ml), and then 4N hydrochloric acid/dioxane (0.38 ml) was added at 0° C., and the mixture was stirred at 0° C. for 15 min. To the reaction solution, ethanol (45 ml) and diisopropyl ether (180 ml) were added, and the mixture was stirred at room temperature for 30 min. The supernatant liquid was separated, and ethanol/diisopropyl ether (1/4 (v/v), 100 ml) was further added to the residue, and the mixture was stirred for 15 min. Then the supernatant liquid was again separated, and the residue was dried under reduced pressure to obtain Compound 1 (880 mg).

The content of 4-(hydroxymethyl)phenol bonded in Compound 1 was determined by analyzing, by HPLC (high performance liquid chromatography), 4-(hydroxymethyl)phenol released by adding 1N sodium hydroxide aqueous solution to Compound 1, agitating the solution at 40° C. for 1 hour and then adding acetic acid to neutralize the solution. As a result, the content of 4-(hydroxymethyl)phenol was determined as 9.1% (w/w), and the proportion of d+e based on d+e+f+g+h+i+j was 22.5%.

According to this method, an isopropylaminocarbonyl-isopropylamino group may be added as $R^5$, and an existing ratio of the group could be determined by $^1$H-NMR (hydrogen nuclear magnetic resonance spectrum) using Compound 1 dissolved in sodium deuteroxide/deuterium oxide/deuterated acetonitrile. The proportion of the isopropylamino-carbonylisopropylamino group in the polyaspartic acid, that is, the proportion of f+g based on d+e+f+g+h+i+j was 7.6%. The remaining aspartic acid residues were in the form of a free carboxylic acid (h+i) or a cyclic structure (j).

Example 2

Synthesis of Compound 2(a conjugate of Compound 1 and doxorubicin)

Compound 1 (500 mg) obtained in Example 1 and disuccinyl carbonate (933 mg) were dissolved in DMF (30 ml), and triethylamine (0.254 ml) was added thereto at 15° C. The mixture was stirred for 20 hours. To the reaction solution, ethanol (90 ml) and diisopropyl ether (360 ml) were added, and the mixture was stirred at room temperature for 30 min. The supernatant liquid was separated, and ethanol/diisopropyl ether (1/4 (v/v), 100 ml) was further added to the residue, and the mixture was stirred for 15 min. Thereafter, the supernatant liquid was again separated, and then the residue was dried under reduced pressure. The thus obtained solid was dissolved in DMF (25 ml), and doxorubicin hydrochloride (116 mg) and triethylamine (0.028 ml) dissolved in DMF (10 ml) were added thereto at 15° C., and the mixture was stirred for 2 hours. To the reaction solution, ethanol (100 ml) and diisopropyl ether (400 ml) were added, and the mixture was stirred at room temperature for 1 hour. The supernatant liquid was separated, and ethanol/diisopropyl ether (1/4 (v/v), 150 ml) was further added to the residue. The mixture was stirred for 15 min. Thereafter, the supernatant liquid was again separated, and the residue was dried under reduced pressure. The resulting solid was dissolved in acetonitrile (30 ml) and water (3 ml), and the solution was applied to a column of an ion exchange resin (5 ml of Dowex 50($H^+$), manufactured by The Dow Chemical Co.) and eluted with acetonitrile/water (10/1 (v/v), 15 ml). To the resulting elution fraction, water (60 ml) was added, and acetonitrile was then distilled off under reduced pressure, followed by lyophilization to obtain Compound 2 (564 mg).

The content of doxorubicin bonded in Compound 2 was determined by analyzing by HPLC (high performance liquid chromatography) an aglycon (adriamycinone) of doxorubicin released by adding 1N hydrochloric acid (1 ml) to Compound 2 (3.38 mg) and agitating the mixture at 40° C. for 1 hour, and comparing the analysis result with a calibration curve of the aglycon obtained by subjecting doxorubicin to the same treatment. As a result, the content of doxorubicin bonded was determined as 11.5% (w/w). In Compound 2, no free doxorubicin was detected.

Gaussian distribution analysis using an aqueous solution of Compound 2 (1 mg/ml) revealed that the average particle diameter is 23 nm (volume weighting). Therefore, Compound 2 was considered to form micelles in water.

Example 3

Synthesis of Compound 3 (a phenyl ester conjugate of a block copolymer consisting of a methoxypolyethylene glycol moiety having a molecular weight of 12,000 and a polyglutamic acid moiety having a polymerization number of 23 and 4-(hydroxymethyl)phenol: in the general formula (IV), $R^8$=Me (a methyl group), $R^9$=a trimethylene group, $R^{10}$=Ac (an acetyl group), $R^{11}$=a 4-(hydroxymethyl)phenoxy group, $R^{12}$=an isopropylaminocarbonylisopropylamino group, k+m+n=23, and b=273)

A methoxypolyethylene glycol-polyglutamic acid block copolymer (a polymerization number of glutamic acid: 23, 1.0 g) prepared by the method according to Japanese Patent Laid-Open No. 5-955 and 4-(tert-butyldimethylsilanyloxymethyl)phenol (295 mg) prepared by the method according to Patent Document 4 were dissolved in DMF (15 ml), and DMAP (19 mg) and DIPC (0.485 ml) were added at 27° C. The mixture was stirred at the same temperature for 20 hours. To the reaction solution, ethanol (23 ml), ethyl acetate (23 ml) and diisopropyl ether (180 ml) were added, and the mixture was stirred at room temperature for 2 hours. Thereafter, the precipitate was collected by filtration and washed with ethanol/diisopropyl ether (1/4 (v/v), 20 ml). The resultant precipitate was dissolved in acetonitrile (15 ml), and 4N hydrochloric acid/dioxane (0.38 ml) was then added at 0° C. The mixture was stirred for 15 min. To the reaction solution, ethanol (45 ml) and diisopropyl ether (180 ml) were added, and the mixture was stirred at room temperature for 30 min. The supernatant liquid was separated, ethanol/diisopropyl ether (1/4 (v/v), 100 ml) was further added to the residue, and the mixture was stirred for 15 min. Thereafter, the supernatant liquid was again separated, and the residue was dried under reduced pressure to obtain Compound 3 (1.1 g).

The content of 4-(hydroxymethyl)phenol bonded in Compound 3 was determined by analyzing by HPLC (high performance liquid chromatography) 4-(hydroxymethyl)phenol released by adding a 1N sodium hydroxide aqueous solution to Compound 3, agitating the mixture at 40° C. for 1 hour and then adding acetic acid to neutralize the solution. As a result, the content of 4-(hydroxymethyl)phenol was determined as 9.4% (w/w), and the proportion of k based on k+m+n was determined as 53.8%.

According to this method, an isopropylaminocarbonyl-isopropylamino group can be added as $R^{12}$, and an existing ratio of the group could be determined by $^1$H-NMR (hydrogen nuclear magnetic resonance spectrum) using Compound 3 dissolved in sodium deuteroxide/deuterium oxide/deuterated acetonitrile. The proportion of the isopropylamino-carbonyl-isopropylamino group to polyglutamic acid, that is, the proportion of m based on k+m+n was 32.0%. The remaining glutamic acid residues were in the form of a free carboxylic acid (n).

Example 4

Synthesis of Compound 4 (a conjugate of Compound 3 and doxorubicin)

Compound 3 (500 mg) obtained in Example 3 and disuccinyl carbonate (966 mg) were dissolved in DMF (30 ml), and triethylamine (0.263 ml) was added at 15° C. The mixture was stirred for 20 hours. To the reaction solution, ethanol (90 ml) and diisopropyl ether (360 ml) were added, and the mixture was stirred at room temperature for 30 min. The supernatant liquid was separated, ethanol/diisopropyl ether (1/4 (v/v), 100 ml) was further added to the residue, and the mixture was stirred for 15 min. Thereafter, the supernatant liquid was again separated, and the residue was dried under reduced pressure. The resulting solid was dissolved in DMF (25 ml), and doxorubicin hydrochloride (120 mg) and triethylamine (0.029 ml) dissolved in DMF (10 ml) were added at 15° C. The mixture was stirred for 2 hours. To the reaction solution, ethanol (100 ml) and diisopropyl ether (400 ml) were added, and the mixture was stirred at room temperature for 1 hour. The supernatant liquid was separated, and ethanol/diisopropyl ether (1/4 (v/v), 150 ml) was further added to the residue, and the mixture was stirred for 15 min. Thereafter, the supernatant liquid was again separated, and the residue was dried under reduced pressure. The resulting solid was dissolved in acetonitrile (30 ml) and water (3 ml), and the resulting solution was applied to a column of an ion exchange resin (5 ml of Dowex 50(H$^+$), made by The Dow Chemical Co.), and eluted with acetonitrile/water (10/1 (v/v), 15 ml). To the resulting elution fraction, water (60 ml) was added, and then, acetonitrile was distilled off under reduced pressure. Thereafter, the resultant fraction was lyophilized to obtain Compound 4 (611 mg).

The content of doxorubicin bonded in Compound 4 was determined by analyzing by HPLC (high performance liquid chromatography) an aglycon (adriamycinone) of doxorubicin released by adding 1N hydrochloric acid (1 ml) to Compound 4 (3.13 mg) and agitating the mixture at 40° C. for 1 hour, and comparing the analysis result with a calibration curve of the aglycon obtained by subjecting doxorubicin to the same treatment. As a result, the content of doxorubicin bonded was determined as 17.1% (w/w). In Compound 4, no free doxorubicin was detected.

Gaussian distribution analysis using an aqueous solution of Compound 4 (1 mg/ml) revealed that the average particle diameter is 43 nm (volume weighting). Therefore, Compound 4 was considered to form micelles in water.

Example 5

Synthesis of Compound 5(a conjugate of Compound 3 and bestatin methyl ester)

Compound 3 (50 mg) obtained in Example 3 and disuccinyl carbonate (97 mg) were dissolved in DMF (3 ml), and triethylamine (0.026 ml) was added at 15° C. The mixture was stirred for 20 hours. To the reaction solution, ethanol (9 ml) and diisopropyl ether (36 ml) were added, and the mixture was stirred at room temperature for 30 min. The supernatant liquid was separated, ethanol/diisopropyl ether (1/4 (v/v), 10 ml) was further added to the residue, and the mixture was stirred for 15 min. Thereafter, the supernatant liquid was again separated, and the residue was dried under reduced pressure. The resulting solid was dissolved in DMF (2 ml), and bestatin methyl ester hydrochloride (8.8 mg) disclosed in Japanese Patent Laid-Open (Kokai) No. 2001-131066 and triethylamine (0.003 ml) dissolved in DMF (0.5 ml) were added at 15° C. The mixture was stirred for 2 hours. To the reaction solution, ethanol (7.5 ml) and diisopropyl ether (30 ml) were added, and the mixture was stirred at room temperature for 1 hour. The supernatant liquid was separated, and ethanol/diisopropyl ether (1/4 (v/v), 10 ml) was further added to the residue. The mixture was stirred for 15 min. Thereafter, the supernatant liquid was again separated, and the residue was dried under reduced pressure. The resulting solid was dissolved in acetonitrile (5 ml) and water (0.5 ml), and the solution was applied to a column of an ion exchange resin (1 ml of Dowex 50(H$^+$), manufactured by The Dow Chemical Co.), and eluted with acetonitrile/water (10/1 (v/v), 3 ml). To the resulting elution fraction, water (6 ml) was added, and then, acetonitrile was distilled off under reduced pressure. Thereafter, the resulting fraction was lyophilized to obtain Compound 5 (55 mg).

The content of bestatin methyl ester bonded in Compound 5 was determined by analyzing by HPLC (high performance liquid chromatography) bestatin methyl ester released by dissolving Compound 5 (4.89 mg) in a 1 mol/l sodium methoxide methanol solution (1 ml) and allowing a reaction at room temperature for 1 hour, and then comparing the analysis result with a calibration curve of bestatin methyl ester. As a result, the content of bestatin methyl ester bonded was determined as 14.6% (w/w). In Compound 5, no free bestatin methyl ester was detected.

Gaussian distribution analysis using an aqueous solution of Compound 5 (1 mg/ml) revealed that the average particle diameter is 41 nm (volume weighting). Therefore, Compound 5 was considered to form micelles in water.

Example 6

Synthesis of Compound 6(a conjugate of Compound 3 and etodolac)

Compound 3 (50 mg) obtained in Example 3 and etodolac (manufactured by Wako Pure Chemical Industries, Ltd., 10.8 mg) were dissolved in DMF (0.5 ml), and DMAP (0.5 mg)

and DIPC (0.012 ml) were added at 15° C. The mixture was stirred for 20 hours. To the reaction solution, ethanol (1.5 ml) and diisopropyl ether (6 ml) were added, and the mixture was stirred at room temperature for 1 hour. Thereafter, the precipitate was collected by filtration and washed with ethanol/diisopropyl ether (1/4 (v/v), 3 ml). The resultant precipitate was dissolved in acetonitrile (3 ml) and water (0.3 ml), and then applied to a column of an ion exchange resin (0.5 ml of Dowex 50($H^+$), manufactured by The Dow Chemical Co.) and eluted with acetonitrile/water (10/1 (v/v), 3 ml). To the resultant elution fraction, water (6 ml) was added, and acetonitrile was distilled off under reduced pressure. Thereafter, the resultant fraction was lyophilized to obtain Compound 6 (56 mg).

The content of etodolac bonded in Compound 6 was determined by analyzing by HPLC (high performance liquid chromatography) etodolac released by dissolving Compound 6 (10.57 mg) in a 1 mol/l sodium hydroxide aqueous solution (10 ml) and allowing the solution to react at room temperature for 1 hour to neutralize the solution with acetic acid, and comparing the analysis result with a calibration curve of etodolac. As a result, the content of etodolac bonded was determined as 11.6% (w/w). In Compound 6, no free etodolac was detected.

Gaussian distribution analysis using an aqueous solution of Compound 6 (1 mg/ml) revealed that the average particle diameter is 49 nm (volume weighting). Therefore, Compound 6 was considered to form micelles in water.

Example 7

Synthesis of Compound 7(a conjugate of Compound 3 and indomethacin)

Compound 3 (50 mg) obtained in Example 3 and indomethacin (manufactured by Wako Pure Chemical Industries, Ltd., 13.5 mg) were dissolved in DMF (0.5 ml), and DMAP (0.5 mg) and DIPC (0.012 ml) were added at 15° C. The mixture was stirred for 20 hours. To the reaction solution, ethanol (1.5 ml) and diisopropyl ether (6 ml) were added, and the mixture was stirred at room temperature for 1 hour. Thereafter the precipitate was collected by filtration and washed with ethanol/diisopropyl ether (1/4 (v/v), 3 ml). The resultant precipitate was dissolved in acetonitrile (3 ml) and water (0.3 ml), and then applied to a column of an ion exchange resin (0.5 ml of Dowex 50($H^+$), manufactured by The Dow Chemical Co.) and eluted with acetonitrile/water (10/1 (v/v), 3 ml). To the resultant elution fraction, water (6 ml) was added, and then, acetonitrile was distilled off under reduced pressure. Thereafter, the resultant fraction was lyophilized to obtain Compound 7 (58 mg).

The content of indomethacin bonded to Compound 7 was determined by analyzing by HPLC (high performance liquid chromatography) a decomposed substance (a 4-chlorobenzoic acid eliminated substance) of indomethacin released by dissolving Compound 7 (8.59 mg) in a 1 mol/l sodium hydroxide aqueous solution (10 ml), allowing the solution to react at room temperature for 1 hour and then neutralizing the solution with acetic acid, and comparing the analysis result with a calibration curve of the same decomposed substance obtained from indomethacin by the same treatment. As a result, the content of indomethacin bonded was determined as 13.3% (w/w). In Compound 7, no free indomethacin was detected.

Gaussian distribution analysis using an aqueous solution of Compound 7 (1 mg/ml) revealed that the average particle diameter is 61 nm (volume weighting). Therefore, Compound 7 was considered to form a micelle in water.

Comparative Example 1

Synthesis of Comparative Compound 1(an amide conjugate of a block copolymer consisting of a methoxypolyethylene glycol moiety having a molecular weight of 5,000 and a polyaspartic acid moiety having a polymerization number of 30 and doxorubicin)

A methoxypolyethylene glycol-polyaspartic acid block copolymer (a polymerization number of aspartic acid: 30, 240 mg) prepared by the method according to Japanese Patent No. 3268913 was dissolved in DMF (10 ml), and N-hydroxysuccinic acid imide (197 mg) and DIPC (0.267 ml) were then added at 35° C. and stirred for 30 min. To the reaction solution, ethyl acetate (20 ml) and diisopropyl ether (100 ml) were added, and the mixture was stirred at room temperature for 1 hour. Thereafter, the precipitate was filtered, washed with ethyl acetate/diisopropyl ether (1/4 (v/v), 10 ml), and dried under reduced pressure. The resultant precipitate was dissolved in DMF (6 ml), and doxorubicin hydrochloride (130 mg) and triethylamine (0.038 ml) dissolved in DMF (6 ml) were added at 25° C. The mixture was stirred for 2 hours. To the reaction solution, ethyl acetate (24 ml) and diisopropyl ether (96 ml) were added, and the mixture was stirred at room temperature for 1 hour. The precipitate was filtered, washed with ethyl acetate/diisopropyl ether (1/4 (v/v), 10 ml), and dried under vacuum. The resultant precipitate was dissolved in acetonitrile (30 ml) and water (3 ml) and then applied to a column of an ion exchange resin (5 ml of Dowex 50($H^+$), manufactured by The Dow Chemical Co.) and eluted with acetonitrile/water (10/1 (v/v), 15 ml). To the resultant elution fraction, water (36 ml) was added, and then, acetonitrile was distilled off under reduced pressure. Thereafter, the resultant fraction was lyophilized to obtain Comparative Compound 1 (338 mg).

The content of doxorubicin bonded in Comparative Compound 1 was determined by analyzing by HPLC (high performance liquid chromatography) an aglycon (adriamycinone) of doxorubicin released by adding 1N hydrochloric acid (1 ml) to Comparative Compound 1 (5.16 mg) and stirring the mixture at 40° C. for 1 hour, and comparing the analysis result with a calibration curve of the aglycon obtained by subjecting doxorubicin to the same treatment. As a result, the content of doxorubicin bonded was determined as 31.6% (w/w). In Comparative Compound 1, no free doxorubicin was detected.

Test Example 1

Drug Release in the Absence of Enzymes (Doxorubicin)

Compound 2 and Compound 4 which are the high-molecular weight conjugates according to the present invention, and Comparative Compound 1 were each dissolved in a concentration of 1 mg/ml in PBS (phosphate-buffered physiological saline, pH: 7.1), and incubated at 37° C. Doxorubicin released from the high-molecular weight conjugate was analyzed and quantified by HPLC in comparison with a calibration curve. The proportion of the quantified value to the total amount of the drug determined from the content of the drug in the high-molecular weight conjugate is shown in FIG. 1.

As is clear from FIG. 1, the high-molecular weight conjugates (Compound 2 and Compound 4) according to the present invention significantly released doxorubicin even in the absence of hydrolyzing enzymes. Particularly Compound 2 having a polyaspartic acid moiety released doxorubicin more rapidly than Compound 4 having a glutamic acid moiety. Incidentally, in Compound 2, the amount of doxorubicin released after 24 hours appeared to be decreased probably because doxorubicin released into the solution was partially degraded in the solution. By contrast, release of doxorubicin from Comparative Compound 1 having the amido bond was not confirmed even after 24 hours. These results indicate an excellent drug release performance of the high-molecular weight conjugate according to the present invention in the absence of hydrolyzing enzymes.

Test Example 2

Drug Release in the Absence of Enzymes (Bestatin methyl ester)

Compound 5 which is a high-molecular weight conjugate according to the present invention was dissolved in PBS (phosphate-buffered physiological saline, pH: 7.1) at a concentration of 1 mg/ml and incubated at 37° C. Bestatin methyl ester released from the high-molecular weight conjugate was analyzed and quantified by HPLC in comparison with a standard curve. The proportion of the quantified value based on the total amount of the drug determined from the drug content in the high-molecular weight conjugate is shown in FIG. 2.

As is clear from FIG. 2, the high-molecular weight conjugate according to the present invention significantly released bestatin methyl ester even without hydrolyzing enzymes. This result indicates the excellent drug release performance of the high-molecular weight conjugate according to the present invention in the absence of hydrolyzing enzymes.

Test Example 3

Drug Release in the Absence of Hydrolyzing Enzymes (Etodolac and Indomethacin)

Compound 6 and Compound 7 were each dissolved in PBS (phosphate-buffered physiological saline, pH: 7.1) at a concentration of 1 mg/ml and incubated at 37° C. Etodolac or indomethacin released from the high-molecular weight conjugate was analyzed and quantified by HPLC in comparison with a calibration curve. The proportion of the quantified value based on the total amount of the drug determined from the drug content of the high-molecular weight conjugate is shown in FIG. 3.

As is clear from FIG. 3, the high-molecular weight conjugate according to the present invention significantly released etodolac or indomethacin even without hydrolyzing enzymes. These results demonstrate an excellent drug release performance of the high-molecular weight conjugate according to the present invention in the absence of hydrolyzing enzymes.

Test Example 4

Antitumor Activity

Mouse colon cancer, Colon 26, maintained by serial subcutaneous subculture in mice, was minced into about 2-mm cubic fragments, and the fragments were subcutaneously transplanted on the dorsal part of female CDF1 mice with a trocar. Eight days after the tumor transplantation, the high-molecular weight conjugate according to the present invention (Compound 2 and Compound 4) or a control drug (Comparative Compound 1 and doxorubicin hydrochloride) was each administered once into the mouse tail vein in a way such that each mouse received the same dose per body weight in terms of doxorubicin. Each compound was dissolved in a 5% liquid glucose for injection and used. After the administration, the major axis (L mm) and the minor axis (W mm) of the tumor were measured using a caliper, and the tumor volume was calculated by the formula (L×W²)/2. Table 1 shows the relative tumor based on the tumor volume on the day of administration.

TABLE 1

|  | Dose | Days after administration |  |  |  |  |
|---|---|---|---|---|---|---|
|  |  | 0 | 3 | 7 | 10 | 14 |
| Compound 2 | 60 mg/kg | 1.00 | 0.73 | 0.22 | 0.22 | 0.72 |
|  | 30 mg/kg | 1.00 | 1.58 | 2.94 | 3.59 | 6.67 |
| Compound 4 | 120 mg/kg | 1.00 | 0.89 | 0.33 | 0.17 | 0.03 |
|  | 60 mg/kg | 1.00 | 1.65 | 1.51 | 0.78 | 0.71 |
|  | 30 mg/kg | 1.00 | 1.96 | 2.76 | 2.17 | 3.44 |
| Comparative Compound 1 | 240 mg/kg | 1.00 | 3.19 | 9.89 | 22.68 | 42.49 |
| Doxorubicin | 15 mg/kg | 1.00 | 1.79 | 3.89 | 5.27 | 12.17 |
| Control |  | 1.00 | 4.37 | 12.55 | 17.94 | 30.69 |

The lethal dose of doxorubicin used as the control drug was 30 mg/kg, and therefore doxorubicin was administered at a dose of 15 mg/kg to perform the antitumor test. As is clear from Table 1, the high-molecular weight conjugate according to the present invention had antitumor activity at a broadened range of the doses and exhibited a higher antitumor effect compared with doxorubicin. By contrast, Comparative Compound 1 exhibited no antitumor effect at all even in a dose of 240 mg/kg.

Figure 1:
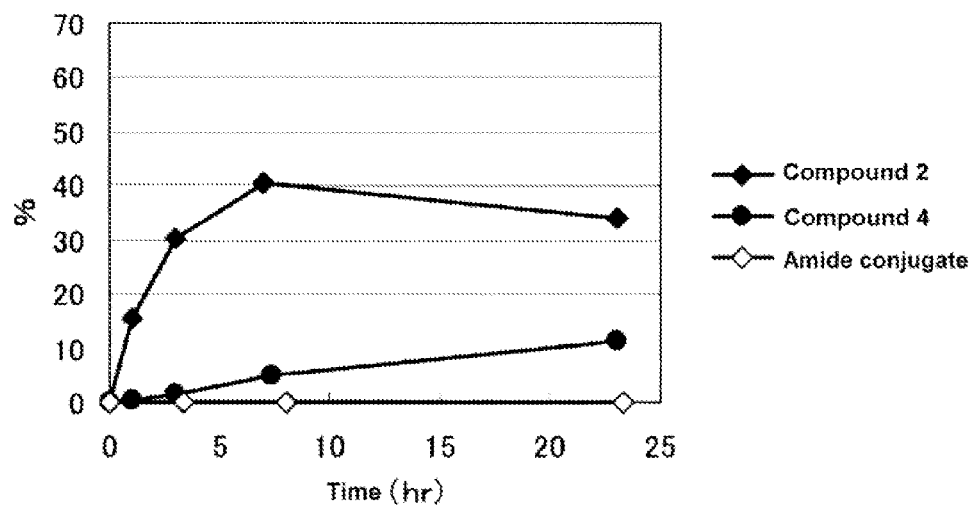
FIG. 1 shows the proportion of the amount of doxorubicin released from Compound 2, Compound 4 and Comparative Compound 1, based on the total amounts of bound doxorubicin in PBS solutions (pH: 7.1, 37° C.).
Figure 2:
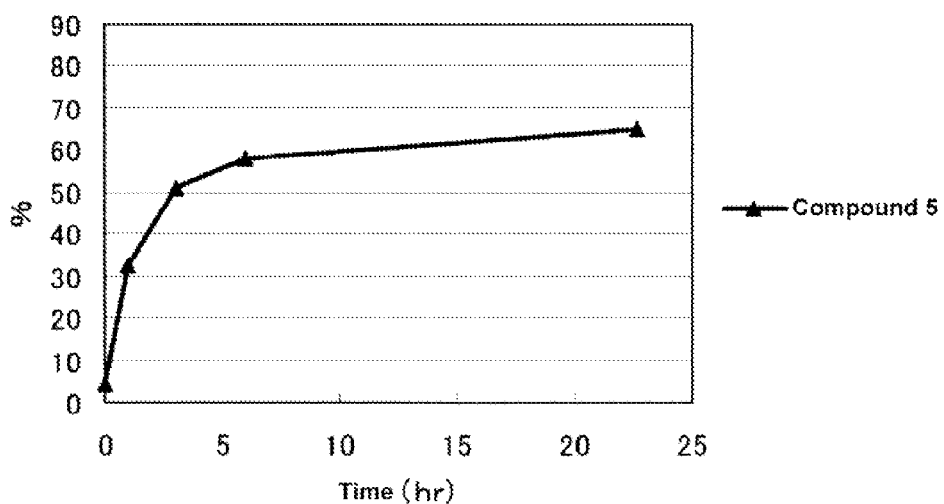
FIG. 2 shows the proportion of the amount of bestatin methyl ester from Compound 5, based on the total amount of bound bestatin methyl ester in a PBS solution (pH: 7.1, 37° C.).
Figure 3:
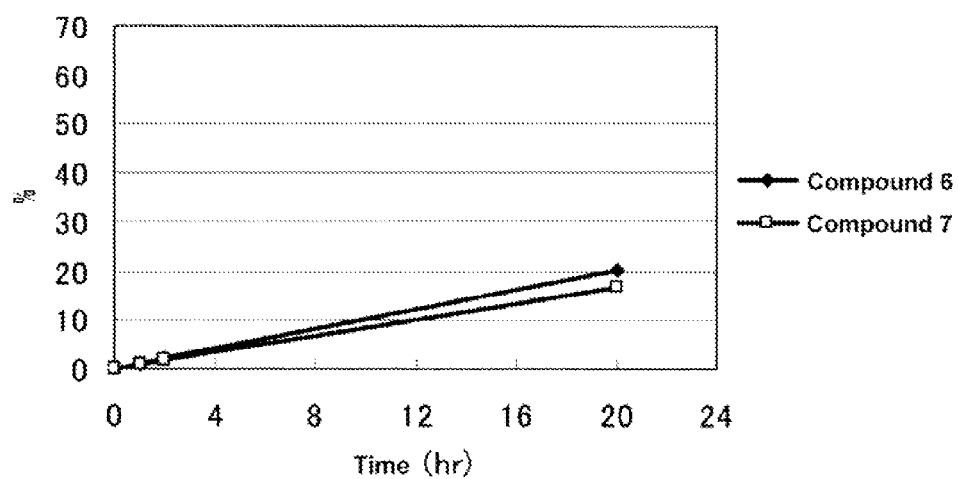
FIG. 3 shows the proportion of the amount of etodolac or indomethacin released from Compound 6 or Compound 7, based on the total amount of the bound etodolac or indomethacin in a PBS solution (pH: 7.1, 37° C.).

The invention claimed is:
1. A high-molecular weight conjugate of physiologically active substances, comprising a structure in which a side chain carboxy group of a block copolymer having a polyethylene glycol moiety and a polyaspartic acid moiety or a polyglutamic acid moiety is bonded to a substituent represented by the general formula (I):

—Ar—CR$^{15}$R$^{16}$—O—C(=O)-A     (I)

wherein Ar represents an aromatic hydrocarbon group optionally having a substituent; R$^{15}$ and R$^{16}$ represent a hydrogen atom; and
—O—C(=O)-A represents a residue of the physiologically active substance wherein the —O—C(=O)— group is bonded to a carbon atom of A.

2. The high-molecular weight conjugate of physiologically active substances according to claim 1, represented by the general formula (II):

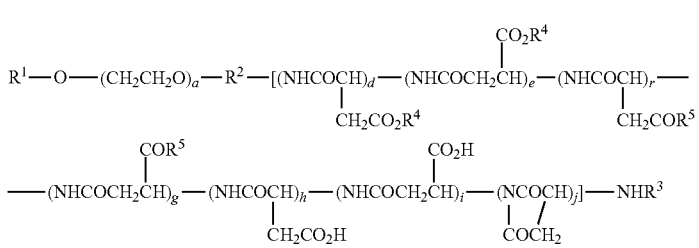

wherein $R^1$ represents a hydrogen atom or a (C1 to C6) alkyl group; $R^2$ represents a linkage group; $R^3$ represents a hydrogen atom or a (C1 to C6) acyl group; $R^4$ represents a substituent represented by the general formula (III):

$$-Ar^1-CR^{17}R^{18}-O-C(=O)\text{-A} \qquad (III)$$

wherein $Ar^1$ represents an aromatic hydrocarbon group optionally having a substituent; $R^{17}$ and $R^{18}$ represent a hydrogen atom; and —O—C(=O)-A represents a residue of the physiologically active substance wherein the —O—C(=O)— group is bonded to a carbon atom of A;

$R^5$ represents a substituent selected from the group consisting of a hydroxymethylphenoxy group optionally having a substituent, a (C1 to C30) alkoxy group, a (C1 to C30) aralkyloxy group, a (C1 to C30) alkylamino group, a di(C1 to C30) alkylamino group, an amino acid with a protected carboxy group, and —$NR^6CONHR^7$ wherein $R^6$ and $R^7$, which may be the same or different from each other, represent a (C3 to C6) cyclic alkyl group or a (C1 to C5) alkyl group which may be substituted with a tertiary amino group; a represents an integer of 5 to 11,500; d, e, f, g, h, i and j each represent an integer of 0 to 200; d+e represents an integer of 1 to 200; and d+e+f+g+h+i+j represents an integer of 2 to 200; and respective units of the polyaspartic acid are bonded in any order.

3. The high-molecular weight conjugate of physiologically active substances according to claim 2, wherein $R^1$ is a (C1 to C3) alkyl group; $R^2$ is a (C2 to C6) alkylene group; $R^3$ is a (C1 to C3) acyl group; $Ar^1$ in the general formula (III) of $R^4$ is a phenyl group in which the bond of $Ar^1$ with a polymer is present in the ortho or para position to the bond with $CR^{17}R^{18}$; and a is an integer of 100 to 300; d, e, f, g, h, i and j are each an integer of 0 to 100; d+e is an integer of 1 to 100; and d+e+f+g+h+i+j is an integer of 6 to 100.

4. The high-molecular weight conjugate of physiologically active substances according to claim 3, wherein $R^1$ is a methyl group; $R^2$ is a trimethylene group; $R^3$ is an acetyl group; $R^{17}$ and $R^{18}$ in the general formula (III) of $R^4$ are both a hydrogen atom; and $R^5$ is —$NR^6CONHR^7$ wherein $R^6$ and $R^7$ are both a cyclohexyl group or an isopropyl group.

5. The high-molecular weight conjugate of physiologically active substances according to claim 1, represented by the general formula (IV):

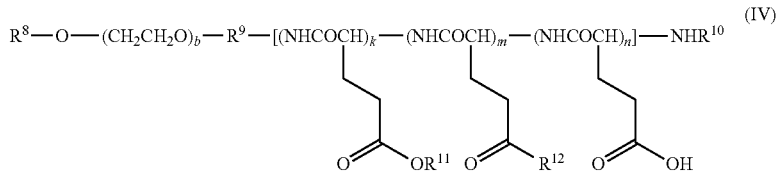

wherein $R^8$ represents a hydrogen atom or a (C1 to C6) alkyl group; $R^9$ represents a linkage group; $R^{10}$ represents a hydrogen atom or a (C1 to C6) acyl group; $R^{11}$ represents a substituent represented by the general formula (V):

$$-Ar^2-CR^{19}R^{20}-O-C(=O)\text{-A} \qquad (V)$$

wherein $Ar^2$ represents an aromatic hydrocarbon group optionally having a substituent; $R^{19}$ and $R^{20}$ represent a hydrogen atom; and —O—C(=O)-A represents a residue of the physiologically active substance wherein the —O—C(=O)13 group is bonded to a carbon atom of A;

$R^{12}$ represents a substituent selected from the group consisting of a hydroxymethylphenoxy group optionally having a substituent, a (C1 to C30) alkoxy group, a (C1 to C30) aralkyloxy group, a (C1 to C30) alkylamino group, a di(C1 to C30) alkylamino group, an amino acid with a protected carboxy group, and —$NR^{13}C0NHR^{14}$ wherein $R^{13}$ and $R^{14}$, which may be the same or different from each other, represent a (C3 to C6) cyclic alkyl group or a (C1 to C5) alkyl group which may be substituted with a tertiary amino group); b represents an integer of 5 to 11,500; k represents an integer of 1 to 200; m and n each represent an integer of 0 to 200; and k+m+n represents an integer of 2 to 200; and respective units of the polyglutamic acid are bonded in any order.

6. The high-molecular weight conjugate of physiologically active substances according to claim 5, wherein $R^8$ is a (C1 to C3) alkyl group; $R^9$ is a (C2 to C6) alkylene group; $R^{10}$ is a (C1 to C3) acyl group; $Ar^2$ in the general formula (V) as $R^{11}$ is a phenyl group in which the bond of $Ar^2$ with a polymer is present in the ortho or para position to the bond with $CR^{19}R^{20}$; and b is an integer of 100 to 300, k represents an integer of 1 to 90, m and n each represent an integer of 0 to 90; and k+m+n is an integer of 6 to 90.

7. The high-molecular weight conjugate of physiologically active substance according to claim 6, wherein $R^8$ is a methyl group; $R^9$ is a trimethylene group; $R^{10}$ is an acetyl group; $R^{19}$ and $R^{20}$ in the general formula (V) of $R^{11}$ are both a hydrogen atom; and $R^{12}$ is —$NR^{13}CONHR^{14}$ wherein $R^{13}$ and $R^{14}$ are both a cyclohexyl group or an isopropyl group.

8. The high-molecular weight conjugate of physiologically active substances according to claim 1, obtained by:
  ester-bonding a side chain carboxy group of a block copolymer having a polyethylene glycol moiety and a polyaspartic acid moiety or a polyglutamic acid moiety to a phenolic hydroxyl group of a hydroxybenzyl alcohol compound; and
  bonding an alcoholic hydroxyl group of the resultant ester compound with a carboxy group of the physiologically active substance.

9. The high-molecular weight conjugate of physiologically active substances according to claim 1, wherein the physiologically active substance is an anticancer agent.

10. The high-molecular weight conjugate of physiologically active substances according to claim 1, wherein the physiologically active substance is a physiologically active peptide.

11. The high-molecular weight conjugate of physiologically active substances according to claim 10, wherein the physiologically active peptide is bestatin or a derivative thereof.

12. The high-molecular weight conjugate of physiologically active substances according to claim 1, wherein the physiologically active substance is an anti-inflammatory agent.

13. The high-molecular weight conjugate of physiologically active substances according to claim 1, wherein the physiologically active substance having a carboxy group is indomethacin, etodolac or a derivative thereof.

14. The high-molecular weight conjugate of physiologically active substances according to claim 1, wherein the high-molecular weight conjugate forms a micelle in water.

15. A pharmaceutical product comprising a high-molecular weight conjugate of physiologically active substances according to claim 1 as an active ingredient.

16. An anticancer agent comprising a high-molecular weight conjugate of physiologically active substances according to claim 9 as an active ingredient.

17. An anti-inflammatory agent comprising a high-molecular weight conjugate of physiologically active substances according to claim 12 as an active ingredient.

18. A method for manufacturing a high-molecular weight conjugate of physiologically active substances according to claim 1, the method comprising
  ester-bonding a side chain carboxy group of a block copolymer having a polyethylene glycol moiety and a polyaspartic acid moiety or a polyglutamic acid moiety to a phenolic hydroxyl group of a hydroxybenzyl alcohol compound; and
  bonding an alcoholic hydroxyl group of the resultant ester compound to a carboxy group of the physiologically active substance, or bonding an alcoholic hydroxyl group of the ester compound with an amino group of the physiologically active substance having the amino group through a carbonyl group.

* * * * *